United States Patent [19]

Agouridas et al.

[11] Patent Number: 5,561,118
[45] Date of Patent: *Oct. 1, 1996

[54] ERYTHROMYCIN COMPOUNDS

[75] Inventors: Constantin Agouridas, Nogent sur Marne; Yannick Benedetti, Rosny sous Bois; Jean-Francois Chantot, Gressy en France; Alexis Denis, Paris; Claude Fromentin, Paris; Odile Le Martret, Paris, all of France

[73] Assignee: Roussel Uclaf, France

[*] Notice: The term of this patent shall not extend beyond the expiration date of Pat. No. 5,444,051.

[21] Appl. No.: 220,484

[22] Filed: Mar. 31, 1994

Related U.S. Application Data

[60] Continuation of Ser. No. 958,235, Oct. 8, 1992, abandoned, which is a division of Ser. No. 793,864, Nov. 18, 1991, abandoned.

[30]  Foreign Application Priority Data

| Nov. 21, 1990 | [FR] | France | 90-14499 |
| May 27, 1991 | [FR] | France | 91-06333 |
| Aug. 29, 1991 | [FR] | France | 91-10728 |

[51] Int. Cl.$^6$ ............................ A61K 31/70; C07H 17/08
[52] U.S. Cl. ............................ 514/29; 536/7.2; 536/7.3; 536/7.4
[58] Field of Search ............................ 536/7.2, 7.3, 7.4; 574/29

[56]  References Cited

U.S. PATENT DOCUMENTS

| 4,680,386 | 7/1987 | Morimoto et al. ............... | 536/7.4 |
| 4,857,641 | 8/1989 | Hauske ............................ | 536/7.3 |

*Primary Examiner*—Elli Peselev
*Attorney, Agent, or Firm*—Bierman & Muserlian

[57] ABSTRACT

Compounds of the formula wherein X and X' form C=O or C=NOR, R is selected from the group consisting of hydrogen, heterocycle, alkyl, alkenyl, alkynyl, all optionally substituted, or X is $$N-R_a, R_b$$

$R_a$ and $R_b$ are hydrogen or a hydrocarbon group or form together with the nitrogen a heterocycle, or with A forms a 9-N, 11-0 ring, and X' is hydrogen, —Y and Y' have the same definition as X and X', B is hydrogen or OR$_4$, R$_4$ is hydrogen or forms together with A a carbonate or a carbamate, A forms with C a double bond or A is OR'$_4$, R'$_4$ is hydrogen or forms together with B a carbonate or A is $$-N(R'_5)(R'_6) \text{ or } -OCH_2-O(CH_2)_n-N(R_9)(R_{10})$$

$R_2$ is alkyl or —CONH$_2$, —CONHCOR$_{11}$ or —CONHSO$_2$R$_{11}$, R$_{11}$ is a hydrocarbon up to 18 carbon atoms, R$_3$ is hydrogen, $$\text{alkyl-}(CH_2)_n-N(R_{12})(R_{13}) \text{ or } -N(R_{14})(R_{15})$$

and Z is hydrogen or a carboxylic acid remainder and their non-toxic, pharmaceutically acceptable acid addition salts, their preparation and intermediates useful as antibiotics.

22 Claims, No Drawings

ERYTHROMYCIN COMPOUNDS

PRIOR APPLICATION

This application is a continuation of U.S. patent application Ser. No. 958,235, filed Oct. 8, 1992, now abandoned, which is a divisional application of U.S. patent application Ser. No. 793,864 filed Nov. 18, 1991, both now abandoned.

STATE OF THE ART

Related prior art includes U.S. Pat. Nos. 3,923,784, 4,670, 549 and 4,826,820, EPA Patents No. 260,938 and No. 194,833, Journal of Medicinal Chemistry, Vol. 17, No. 9 (Sept. 1974), p. 953 to 956 and Journal of Antibiotics, Vol. 43, No. 5 (May, 1990), p. 570 to 573.

OBJECTS OF THE INVENTION

It is an object of the invention to provide the novel compounds of formula I and their non-toxic, pharmaceutically acceptable acid addition salts and a novel process and intermediates for their preparation.

It is a further object of the invention to provide novel antibiotic compositions and a method of combatting bacterial infections in warm-blooded animals.

These and other objects and advantages of the invention will become obvious from the following detailed description.

THE INVENTION

The novel compounds of the invention are selected from the group consisting of a compound of the formula

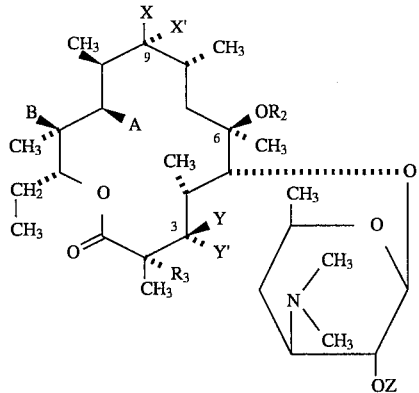

I wherein X and X' together with the carbon atom to which they are attached is —C=O or C=NOR, R is selected from the group consisting of a) hydrogen, b) mono or bicyclic, saturated or unsaturated, aromatic or non-aromatic heterocyclic containing at least one nitrogen atom and optionally another heteroatom and containing up to 12 links optionally substituted on the nitrogen atom with alkyl of 1 to 4 carbon atoms, c) linear, branched or cyclic alkyl, alkenyl or alkynyl of up to 18 carbon atoms optionally substituted by at least one member of the group consisting of —OH, halogen, cyano, nitro, amidinyl, guanidinyl, heterocyclic as defined above, alkoxy, alkenyloxy and alkynyloxy of up to 6 carbon atoms, alkylthio, alkenylthio and alkynylthio of up to 6 carbon atoms, the sulfur atom being optionally oxidized into sulfoxide or sulfone, aryl, aralkyl, aryloxy, aralkoxy, arylthio, aralkylthio, the sulfur atom being optionally oxidized into sulfoxide or sulfone, each of said alkoxy, alkenyloxy, alkynyloxy, alkylthio, alkenylthio or alkynylthio, aryl, aralkyl, aryloxy, aralkoxy, arylthio or aralkylthio being optionally substituted by at least one member of the group consisting of hydroxy, alkoxy and alkylthio of 1 to 6 carbon atoms, alkenylthio and alkynylthio of up to 6 carbon atoms, amino, monalkylamino of 1 to 6 carbon atoms, dialkylamino of up to 12 carbon atoms, amidinyl, guanidinyl, heterocycle as defined above, aryl, aryloxy, arylthio, aralkyl, aralkoxy and aralkylthio also optionally substituted by a member of the group consisting of methyl, ethyl, propyl, carbamoyl, aminomethyl, dimethylaminomethyl, aminoethyl, dimethylaminoethyl, carboxyl, methoxycarbonyl, ethoxycarbonyl, d)

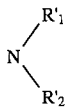

wherein either $R'_1$ and $R'_2$ are individually selected from the group consisting of hydrogen, alkyl, cycloalkyl, alkenyl or alkynyl of up to 18 carbon atoms, aryl or aralkyl, each of $R'_1$ and $R'_2$ being optionally substituted by at least one member of the group consisting of hydroxy, alkoxy, alkenyloxy, alkynyloxy, alkylthio, alkenylthio or alkynylthio of up to 8 carbon atoms, amino, monoalkylamino of up to 4 carbon atoms, dialkylamino of up to 8 carbon atoms, cyano, free, esterified or salified carboxyl, acyl or carbamoyl of up to 8 carbon atoms, $Si(alk)_3$ and $Si(Oalk)_3$ alk is alkyl of up to 4 carbon atoms, heterocycle as defined above, or $R'_1$ and $R'_2$ together with the nitrogen atom to which they are attached form a mono or bicyclic saturated or unsaturated, aromatic or non-aromatic heterocycle optionally containing another heteroatom, and containing up to 12 links; quaternary ammonium, 1,2-epoxyethyl, 2,2-dimethyl-1-2-epoxyethyl and a resulting group from the opening with a nucleophile reagent, thereof,

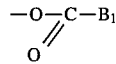

$B_1$ is alkyl or alkoxy of up to 6 carbon atoms, or aryl, aralkyl, aryloxy or aralkoxy, free or protected formyl, free, esterified or salified carboxyl, thiocyanate, acyl, carbamoyl and —$(CH_2)_n R'$, R' is the remainder of an amino acid, and n is an integer between 0 and 6, or X is

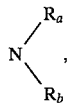

$R_a$ and $R_b$ are individually selected from the group consisting of a) hydrogen, b) hydrocarbon of up to 18 carbon atoms optionally containing at least one heteroatom and optionally substituted by at least one functional group, c) mono or bicyclic, saturated or unsaturated, aromatic or non-aromatic heterocycle with at least one nitrogen atom and optionally another heteroatom chosen from oxygen, sulfur and nitrogen and containing up to 12 links and optionally substituted on the nitrogen by alkyl of 1 to 4 carbon atoms, or $R_a$ and $R_b$ together with the nitrogen atom to which they are attached form a mono or bicyclic, saturated or unsaturated, aromatic or non-aromatic heterocycle containing at least one nitrogen atom and optionally another heteroatom chosen from oxygen, sulfur and nitrogen and containing up to 12 links or $R_a$ and $R_b$ form with A a 9-N, 11-0 ring, and X' is hydrogen, Y and Y' individually have the meaning of X and X', B is hydrogen or $OR_4$, $R_4$ is hydrogen, or forms with A a carbonate or carbamate, A forms with the carbon which carries it and the carbon in position 10 a double bond, or A is OR'$_4$, R'$_4$ is hydrogen, or forms with B a carbonate, or A is NR'$_5$, R'$_5$ is C=O forming with B a carbamate group, R'$_6$ is hydrogen R'$_6$ or alkyl, aralkyl or alkoxy of up to 12 carbon atoms or

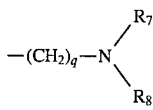

R$_7$ and R$_8$ are individually hydrogen or alkyl or aralkyl of up to 18 carbon atoms, or form together with the nitrogen a heterocycle as defined above, q is an integer between 1 and 6, or A is

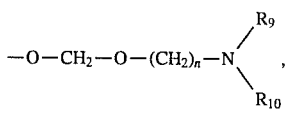

R$_9$ and R$_{10}$ are hydrogen or alkyl of 1 to 8 carbon atoms, or form together with the nitrogen a heterocycle as defined above, n is an integer between 1 and 6, R$_2$ is selected from the group consisting of alkyl of 1 to 8 carbon atoms, —CONH$_2$, —CONHCOR$_{11}$ and —CONHSO$_2$R$_{11}$, R$_{11}$ is a hydrocarbon of 1 to 18 carbon atoms optionally containing at least one heteroatom, R$_3$ in alpha or beta position is selected from the group consisting of a) hydrogen, b) alkyl of 1 to 8 carbon atoms, c)

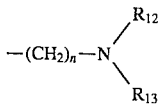

R$_{12}$ and R$_{13}$ are selected from the group consisting of hydrogen, alkyl of 1 to 8 carbon atoms or form with the nitrogen atom a heterocycle as defined above, n is an integer between 1 and 6 and d)

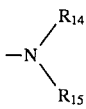

R$_{14}$ and R$_{15}$ are individually hydrogen or alkyl of 1 to 8 carbon atoms or a heteroatom or alkyl or alkoxy of 1 to 8 carbon atoms, Z is hydrogen or the remainder of a carboxylic acid of 1 to 18 carbon atoms, the oximes that can be represented by X and X' or Y and Y' can be of syn or anti configuration and their non-toxic, pharmaceutically acceptable acid addition salts.

Examples of suitable heterocycles are pyrrolyl, pyrrolidinyl, pyridyl, pyrazinyl, pyrimidyl, piperidinyl, piperazinyl, quinuclidinyl, oxazolyl, isoxazolyl, morpholinyl, indolyl, imidazolyl, benzimidazolyl, triazolyl, thiazolyl, azetidinyl and aziridinyl. Examples of the alkyl, alkenyl or alkynyl are preferably methyl, ethyl, propyl, isopropyl, n-butyl, isobutyl, tert-butyl, decyl or dodecyl, vinyl, allyl, ethynyl, propynyl, cyclobutyl, cyclopentyl or cyclohexyl. The halogen is preferably fluorine, chlorine or bromine. The aryl is preferably phenyl and the aralkyl is preferably (C$_6$H$_5$)—(CH$_2$)$_a$, a being an integer between 1 and 6, for example the number 1, 2, 3 or 4, or naphtyl. The alkoxy is preferably methoxy, ethoxy, propoxy, isopropoxy, n-butyloxy, isobutyloxy, tert-butyloxy, n-pentyloxy, isopentyloxy, sec-pentyloxy, tertpentyloxy, neopentyloxy, n-hexyloxy, sec-hexyloxy, or tert-hexyloxy. The corresponding alkylthio can be used by taking the same values and replacing the oxygen by a sulfur, for example: methylthio, ethylthio. Furthermore, the sulfur atom can be oxidized, for example: methylsulfinyl, methylsulfonyl.

The alkenyloxy is preferably vinyloxy, 1-propenyloxy, allyloxy, 1-butenyloxy, 2-butenyloxy, 3-butenyloxy, 2-methyl-1-butenyloxy, pentenyloxy, hexenyloxy or 3-methylbutenyloxy and the corresponding alkenylthio can be used by taking the same values and replacing the oxygen by an optionally oxidized sulfur. The alkynyloxy is preferably ethynyloxy, propargyloxy, propynyloxy, butynyloxy, pentynyloxy or hexynyloxy and the corresponding alkynylthio can be used by taking the same values and replacing the oxygen by an optionally oxidized sulfur.

The aryloxy is preferably phenoxy, thienyloxy, furyloxy, thiazolyloxy, thiadiazolyloxy, oxazolyloxy, tetrazolyloxy, pyrrolyloxy, imidazolyloxy, pyrazolyloxy, isothiazolyloxy, isoxazolyloxy, triazolyloxy, thiatriazolyloxy, pyridyloxy, as well as the following condensed groups: benzothienyloxy, benzofuryloxy, indolyloxy and benzimidazolyloxy. The corresponding optionally oxidized arylthio groups can be used, for example: phenylthio, phenylsulfonyl, phenylsulfinyl. The aralkoxy is preferably benzyloxy, phenylethyloxy, phenylpropyloxy, thienylmethyloxy, thienylethyloxy, thienylpropyloxy, furfuryloxy, furylethyloxy, furylpropyloxy, thiazolylmethyloxy, thiazolylethyloxy, tetrazolylmethyloxy, thiadiazolyl-methyloxy or thiadiazolylethyloxy. The corresponding optionally oxidized aralkylthio groups can of course be used.

Among the protected formyl groups, the preferred are the acetal-type such as 1,3-dioxolan-2-yl, dimethoxymethyl or diethoxymethyl. Esterified carboxyl may be alkoxycarbonyl of at most 7 carbon atoms such as methoxycarbonyl, ethoxycarbonyl, propoxycarbonyl, isopropoxycarbonyl or butoxycarbonyl. Also to be mentioned are alkoxyalkoxycarbonyl such as methoxymethoxycarbonyl, isopropoxymethoxycarbony alkylthiomethoxycarbonyl such as methylthiomethoxycarbonyl, isopropylthiomethoxycarbonyl, acyloxyalkoxycarbonyl such as pivaloyloxymethoxycarbonyl and acetoxyethoxycarbony Among the salts formed with the carboxyl group are sodium, potassium, lithium, calcium, magnesium, and ammonium salts or the salts formed with amino organic bases such as trimethylamine, diethylamine, triethylamine, tris(hydroxymethyl) aminomethane. Among the acyl are acetyl, propionyl, butyryl, isobutyryl, n-valeryl, isovaleryl, tert-valeryl and pivalyl.

Examples of suitable acids to form the acid addition salts a re inorganic acids such as hydrochloric acid, nitric acid, phosphoric acid or sulfuric acid and organic acids such as propionic acid, trifluoroacetic acid, maleic acid, tartaric acid, methanesulfonic acid, benzenesulfonic acid, p-toluenesulfonic acid, stearic acid, ethylsuccinic acid or laurylsulfuric acid.

Among the preferred compounds of formula I are those wherein

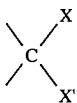

is C=NOR with R having the above definition, those wherein R is alkyl of 1 to 6 carbon atoms substituted with

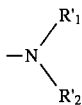

wherein R'₁ and R'₂ have the above definition such as

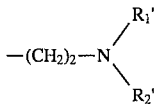

and R'₁ and R'₂ are alkyl of 1 to 4 carbon atoms such

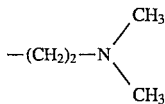

or R'₁ is hydrogen and R'₂ is alkyl of 1 to 4 carbon atoms substituted with a heterocycle with at least one nitrogen, preferably

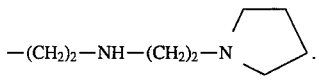

Also preferred compounds of formula I are those wherein R is alkyl of 1 to 6 carbon atoms substituted with alkoxy of 1 to 6 carbon atoms optionally substituted with methoxy such as —CH₂O—CH₂—CH₂—O—CH₃ and those wherein R is a heterocycle containing at least one nitrogen such as 3-piperidinyl. Also referred are compounds wherein

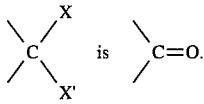

Among the preferred compounds of the invention are the compounds of formula I wherein X and X' and Y and Y' together form C=O, the compounds of formula I wherein Y and Y' together form C=NOR, R being as defined above and especially benzyl, the compounds of formula I wherein R₂ is alkyl of 1 to 4 carbon atoms, for example methyl, the compounds of formula I wherein R₃ is hydrogen, (α or β), the compounds of formula I wherein A is —OH, the compounds of formula I wherein B is —OH, the compounds of formula I wherein A and B form a cyclic 11,12-carbonate, the compounds of formula I wherein A and B form

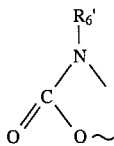

R'₆ is hydrogen or alkyl, aralkyl or alkoxy of up to 12 carbon atoms or

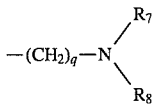

R₇ and R₈ are individually hydrogen or alkyl or aralkyl of up to 18 carbon atoms, or form with the nitrogen atom a heterocycle as defined above, and q is an integer between 1 and 6.

Among these compounds, there can be mentioned more particularly the compounds in which R'₆ is aralkyl of up to 12 carbon atoms, for example —(CH₂)₄C₆H₅.

Among the more preferred compounds of the invention are those wherein Z is hydrogen and especially those of examples 1, 2, 3, 7, 10, 13, 36 and 37.

The novel antibiotic compositions of the invention are comprised of at least one compound of formula I and their non-toxic, pharmaceutically acceptable acid addition salts and an inert pharmaceutical carrier or excipient. The compositions maybe in the form of tablets, dragees, gelules, capsules, granules, suppositories, creams, gels, ointments and injectable solutions or suspensions or powders to be dissolved extemporaneously in appropriate solvents such as apyrogenic sterile water.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention possess a very good antibiotic activity on gram ⊕ bacteria such as staphylococci, streptococci, pneumococci and can therefore be used as medicaments in the treatment of sensitive germ infections and, notably, in that of staphylococcia such as staphylococcic septicemias, malignant staphylococcia of the face or skin, pyodermatitis, septic or suppurating sores, boils, anthrax, phlegmon, erysipelas and acne, staphylococcia such as primary or post-influenzal acute angina, bronchopneumonia, pulmonary suppurations, streptococcia such as acute angina, otitis, sinusitis, scarlet fever, pneumococcia such as pneumonia, bronchitis; the brucellosis, diphtheria, gonococcal infections. The products of the present invention are also active against infections due to germs such as *Haemophilus influenzae*, Rickettsies, *Mycoplasma pneumoniae,* Chlamydia, Legionella, Ureaplasma and Toxoplasma.

The novel method of the invention for treating bacterial infections in warm-blooded animals, including humans, comprises administering to warm-blooded animals an antibacterially effective amount of at least one compound of formula I and its non-toxic. pharmaceutically acceptable acid addition salts. The compounds be administered orally, rectally, parenterally or topically on the skin or mucous membranes, but preferably orally. The usual daily dose is 1.5 to 6 mg/kg depending on the condition treated, the method of administration and the particular compound used. For example, the product of Example 1 may be orally administered at a dose of 1.5 to 6 mg/kg.

The process of the invention for the preparation of a compound of formula I comprises reacting a compound of the formula

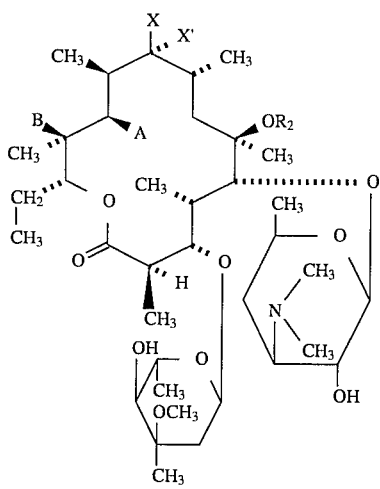

II wherein X, X', B and A have the above definitions with an acid in an aqueous medium to obtain a compound of the formula

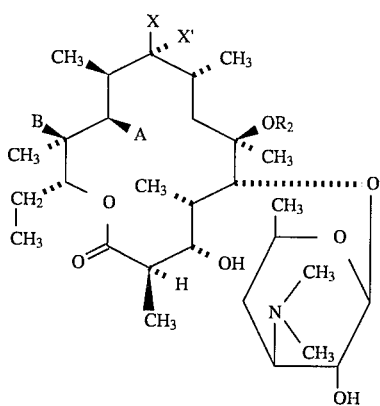

III subjecting the latter to the action of a blocking agent of the 2'-hydroxyl to obtain a compound of the formula

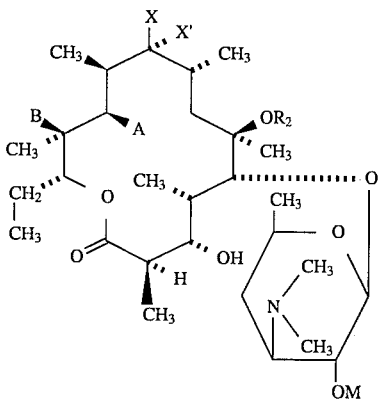

IV wherein OM is a blocked hydroxyl, and the other substituents have the above definitions, subjecting the latter to an oxidizing agent of 3-hydroxyl to obtain a compound of the formula

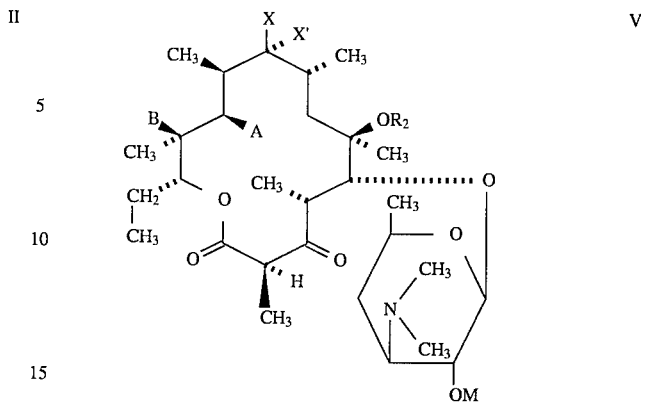

V optionally subjecting the latter to the action of a reagent capable of introducing $R'_3$, $R'_3$ having the same value as $R_3$ with the exception of hydrogen, then either optionally to the action of a releasing agent of the 2'-hydroxyl to obtain a compound of the formula

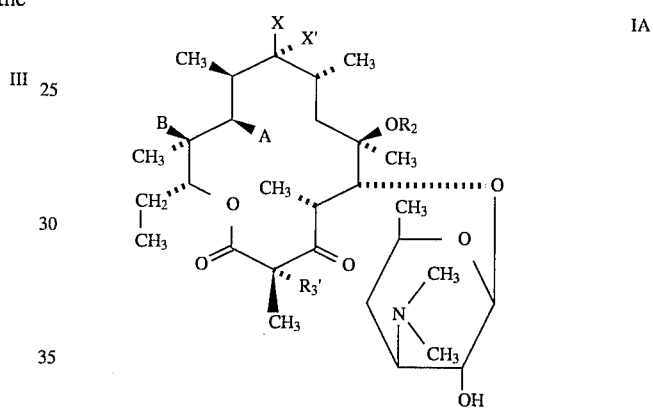

IA wherein Y and Y' form with the carbon atom to which they are linked a ketone and optionally subjecting the latter to the action of an oximation agent of the ketone or beta keto ester to obtain the desired compound of formula I and optionally subjecting the latter to the action of an esterification agent of 2'-hydroxyl, or first to the action of an oximation agent of the ketone or beta-keto ester, and then optionally to the action of a releasing agent of the 2'-hydroxyl to obtain the desired compound of formula I and optionally subjecting the latter to the action of an acid to form the salt.

In a preferred embodiment of the process of the invention, the hydrolysis of the cladinose is carried out with aqueous hydrochloric acid or in methanol and the blocking of the 2'-hydroxyl is carried out using an acid or a functional acid derivative, for example an acid anhydride or an acid halide, or silicon derivatives. Depending upon the blocking agent used, the products of formula V may or may not be the products of formula I. The introduction of $R'_3$ is carried out by methods known to a man skilled in the art, for example, with a halide.

The release of the 2'-hydroxyl is carried out by methanolysis and the oxidation of the hydroxyl is carried out either with chromic anhydride in dilute sulfuric acid according to the Jones oxidation reaction, or diimides in the presence of dimethylsulfoxide (DMSO). The oximation of the ketone function can be effected in the single stage using an $RONH_2$ hydroxylamine carrying the desired R or using H₂N—O—(CH₂)ₙ—Hal hydroxylamine to obtain a compound of formula I in which

is =N—O—(CH₂)ₙ-Hal and optionally subjecting the latter to the action of an amine of the formula

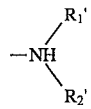

wherein $R'_1$ and $R'_2$ have the above meaning to obtain a a compound of formula I in which

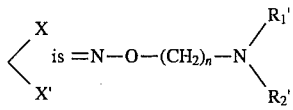

and optionally converting the latter for example by an alkylation, acylation, or reduction agent to obtain the desired compound of formula I. The esterification in position 2' is carried out according to standard processes and the salification is carried out using acids according to standard processes.

The compounds of formula II used as starting products are prepared from known products described in European Patents No. 0,216,169, No. 41,355 and No. 0,180,415 using the processes described hereafter in the experimental part. 6-O-methyl erythromycin oxime is described, for example, in EP 0,180,415.

Also a subject of the invention is a variant of the preceding process where the different stages are carried out in a different order.

In a variation of the process for preparing products of formula I in which X and X' form C=NOR, the product of formula IV_A in which X and X' are C=N—OR is prepared from the corresponding ketone of formula II by the action of NH₂OR in an acid medium to obtain according to the pH of the reaction, the corresponding product of formula IV_A saturated or unsaturated in position 10(11):

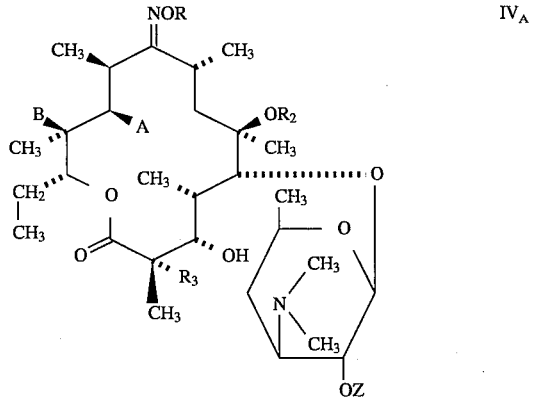

A being OH if there is no unsaturation in position 10(11) or being hydrogen if there is an unsaturation in position 10(11), R, R₂, B and Z having the above meaning.

In another variation of the process for preparing compounds of formula I in which X and X' are C=NOR, R being defined as above, a compound of formula $I_A$ in which X and X' form a keto is subjected to the action of a compound of the formula NH₂OR to obtain the corresponding compound of formula I, in which X and X' are C=NOR and Z is hydrogen and optionally the compound is esterified or salified.

The intermediate products obtained during the implementation of the process of the invention and the product of formula II are new and are an object of the present invention.

In the following examples, there are described several preferred embodiments to illustrate the invention. However, it is to be understood that the invention is not intended to be limited to the specific embodiments.

EXAMPLE 1

9-[O-[2-[(dimethylamino)-ethyl]-oxime] of 3 de [(2,6-dideoxy-3-C-methyl-3-O-methyl-α-L-ribo-hexopyranosyl)-oxy]-6-O-methyl-3-oxo erythromycin Step A: 9-[O-2-(dimethylamino)-ethyl]-oxime] of 3-O-de(2, 6-dideoxy- 3-C-methyl-3-O-methyl-α-L-ribo-hexopyranosyl)-6-O-methyl erythromycin.

100 mg of the product of Preparation 1 and 0.3 ml of a solution of 22° Be hydrochloric acid were suspended in 3 ml of water and the mixture was stirred for 3 hours at ambient temperature. The solution was adjusted to a basic pH by adding a few drops of 20% ammonium hydroxide and 2 ml of a saturated solution of sodium chloride were added. Extraction took place with ethyl acetate and chloroform and after drying, the solvents were evaporated. The residue was chromatographed on silica eluting first with pure ethyl acetate, then with an ethyl acetate-triethylamine (98/2) mixture to obtain 50 mg of the desired product.

ANALYSES

IR: (Nujol on Nicolet) CO: 1733 cm⁻¹

MS (FAB) (M+H)⁺=676⁺

Step B: 2'-O-acetyl 9-[O-[2-(dimethylamino)-ethyl]-oxime] of 3-de[(2,6'dideoxy-3-C-methyl-3-O-methyl-α-L-ribo-hexopyranosyl)]-6-O-methyl- 3-oxo erythromycin.

150 mg of the product of Step A, 38 mg of potassium carbonate and 33 microliters of acetic anhydride were suspended in 2 ml of acetone and the suspension was stirred for 20 hours. 1 ml of ice was added, followed by stirring for 5 minutes and saturation with sodium chloride. 1 ml of water was added, followed by extraction with ethyl acetate, drying on magnesium sulfate and the solvents were evaporated off to obtain 110 mg of crude product which was chromatographed on silica, eluting with an ethyl acetate-triethylamine mixture (96/4) to obtain 110 mg of the desired product.

MS (FAB) (M+H)⁺=718⁺

Step C: 9-[O-[2-(dimethylamino)-ethyl]-oxime] of 3-de[(2, 6-dideoxy- 3-C-methyl-3-O-methyl-α-L-ribo-hexopyranosyl)-oxy]-6-O-methyl- 3-oxo erythromycin.

Step C1: Oxidation 110 mg of the product of Step B, 0.21 ml of dimethylsulfoxide and 165 mg of 1-[3-(dimethylamino)-propyl]-3-ethyl-carbonamide hydrochloride (EDAC) were dissolved in 2 ml of methylene chloride under an argon atmosphere and the solution was stirred for 20 minutes after which 165 mg of pyridinium trifluoroacetate were added. After 2 hours, 70 microliters of dimethylsulfoxide and 55 mg of EDAC were added and the mixture was stirred for 20 minutes after which 55 mg of pyridinium trifluoroacetate were added. 2 ml of water were added to the solution and after stirring for 10 minutes, the solution was taken up in methylene chloride, washed with water and dried on magnesium sulfate. The solvents were evaporated to obtain 240 mg of crude product which was chromatographed on silica eluting with a mixture of ethyl acetate and triethylamine (95/5) to obtain 85 mg of the desired product.

Step C2: Releasing the hydroxyl in position 2'

85 mg of the product of Step C1 were dissolved in 3 ml of methanol and the solution was stirred for 24 hours. The solvent was evaporated under reduced pressure to obtain a residue which was purified by chromatography eluting with a mixture of ethyl acetate-triethylamine (95/5) to obtain 75 mg of the desired product.

ANALYSES

IR: ($CHCl_3$ on Nicolet) OH: 3606, 3510, 3415 $cm^{-1}$ C=O: 1744, 1714 $cm^{-1}$ UV: max 287 nm $\epsilon$=10900 MS: (FD) $M^+$=673$^+$ NMR: ($CDCl_3$, 400 MHz, $\delta$ ppm) 3.86 ($H_2$), 3.12 ($H_4$), 4.31 ($H_5$), 1.39 ($CH_3$ in position 6), 2.74 ($OCH_3$ in position 6), 3.56 ($H_8$), 2.5–2.65 ($H_{10}$, $CH_2$—N), 3.89 ($H_{11}$), 1.22 (12-$CH_3$), 5.17 ($H_{13}$), 0.86 ($H_{15}$), 4.09 (O—$\underline{CH_2}$—$CH_2$), 2.27 ($CH_3$—N), 0.97–1.16–1.26–1.3–1.32 ($CH_3$), 4.31 (H'$_1$), 3.19 (H'$_2$), 2.5 (H'$_3$), 3.64 (H'$_5$). Specific rotation was $[\alpha]_D$=+4° (c=0.5% in $CHCl_3$).

PREPARATION 1: 9-[O-[2-(dimethylamino)-ethyl]-oxime] of 6-O-methyl erythromycin.

160 mg of chloro-2-N,N-dimethylamine hydrochloride were dissolved in 1.5 ml of dimethylsulfoxide under a nitrogen atmosphere and 60 mg of sodium hydride at 50% in oil were added. The mixture was stirred for 30 minutes under a nitrogen atmosphere and 380 mg of 6-O-methyl erythromycin 9-oxime, 0.5 ml of tetrahydrofuran and 30 mg of sodium hydride were added. The solution was kept for 4 hours under a nitrogen atmosphere and then a few drops of a saturated solution of ammonium chloride were added. 20 ml of ethyl acetate were added, followed by washing with a saturated aqueous solution of sodium bicarbonate, then with a saturated aqueous solution of sodium chloride. After drying on magnesium sulfate, the solvents were evaporated off. The residue was chromatographed on silica eluting with a mixture of chloroform, methanol, ammonium hydroxide 97/7/0.5 to obtain 200 mg of the desired product with a specific rotation of $[\alpha]_D$=–99° (c=1% in chloroform).

IR Spectrum: ($CHCl_3$) OH: 3600 $cm^{-1}$ C=O: 1728 $cm^{-1}$ C=N: 1626 $cm^{-1}$ Mass spectrum: (FAB) $(M+H)^+$=834$^+$

EXAMPLE 2

9-[O-[2-methoxy ethoxy)-methyl]-oxime] of 3-de[(2,6-dideoxy-3-C-methyl-3-O-methyl-α-L-ribo-hexopyranosyl)-oxy]-6-O-methyl-3-oxo erythromycin Step A: 9-[O-[2-methoxy-ethoxy)-methyl]-oxime] of 3-O-de(2,6-dideoxy- 3-C-methyl-3-O-methyl-α-L-ribo-hexopyranosyl)-6-O-methyl erythromycin.

Using the procedure of Example 1, Step A, 1.7 g of the product of Preparation 2 were reacted to obtain 1.25 g of the desired product with a specific rotation of $[\alpha]_D$=–28°±1.5° (c=0.95% in $CHCl_3$).

IR Spectrum: ($CHCl_3$ on Nicolet) OH: 3420 $cm^{-1}$ C=O: 1725 $cm^{-1}$ C=N: 1636 $cm^{-1}$ Mass Spectrum: (FAB) $(M+H)^+$=693$^+$ Step B: 9-[O-[(2-methoxy-ethoxy)-methyl]-oxime] of 2'-O-acetyl-3-de( 2,6-dideoxy-3-C-methyl-3-O-methyl-α-L-ribo-hexopyranosyl, 6-O-methyl erythromycin.

Using the procedure of Example 1, Step B, 346 mg of the product of Step A were reacted to obtain 351 mg of the desired product.

ANALYSES

IR: ($CHCl_3$ on Nicolet) OH: 3620, 3600 $cm^{-1}$ C=O: 1730 $cm^{-1}$

MS: (FAB) $(M+H)^+$=735$^+$ $[\alpha]_D$=–52.5°±1° (c=1% in $CHCl_3$)

Step C: 9-[O-[2-methoxy-ethoxy)-methyl]-oxime] of 2'-O-acetyl-3-de( 2,6-dideoxy-3-C-methyl-3-O-methyl-α-L-ribo-hexopyranosyl)-oxy]- 6-O-methyl-3-oxo erythromycin.

4 g of the product of Step B and 2.71 ml of Jones reagent were dissolved in 100 ml of acetone and the reaction mixture was stirred for 1 hour at 0° C. 10 ml of 1-propanol were added and the mixture was stirred at 0° C. for 20 minutes. The acetone was evaporated off under reduced pressure and the residue was taken up in 50 ml of methylene chloride and 20 ml of water. The mixture was adjusted to pH 8 with potassium carbonate and extraction took place with methylene chloride, followed by washing with water, drying over magnesium sulfate, filtering, then evaporating to dryness under reduced pressure to obtain 4.5 g of product which was chromatographed on silica (eluant: ethyl acetate—triethylamine 98-2) to obtain 2.45 g of the desired product.

IR Spectrum: ($CHCl_3$ on Nicolet) C=N: 1630 $cm^{-1}$ C=O: 1742, 1716 $cm^{-1}$ OH: 3510, 3410 $cm^{-1}$ Step D: 9-[O-[(2-methoxy-ethoxy)-methyl]-oxime] of 3-de [(2,6-dideoxy- 3-C-methyl-3-O-methyl-α-L-ribo-hexopyranosyl)-oxy]-6-O-methyl- 3-oxo erythromycin.

Using the procedure of Step C2 of Example 1, 300 mg of the product of Step C were reacted to obtain 0.27 g of the desired product.

ANALYSES

IR: ($CHCl_3$ on Nicolet) OH: 3430, 3505 $cm^{-1}$ C=O: 1744, 1714 $cm^{-1}$

NMR: ($CDCl_3$, 400 MHz) 0.86 ppm (ethyl $CH_3$), 1.00–1.17 ppm 1.26–1.30–1.32 ppm ($CH_3$ non attributed), 1.23 ppm ($CH_3$ in position 12), 1.38 ppm ($CH_3$ in position 6), 2.37 ppm (N($CH_3$)2), 2.61 ppm ($H_{10}$ and H$_3$'), 2.73 ppm ($OCH_3$ in position 6), 3.13 ppm (H4), 3.26 ppm (H$_2$'), 3.38 ppm ($OCH_3$ of MEM), 3.53 ppm, 3.76 ppm ($OCH_2CH_2O$ of MEM), 3.59 ppm (H$_5$'), 3.70 ppm ($H_8$), 3.86 ppm ($H_2$), 3.91 ppm ($H_{11}$), 4.33 ppm (H$_1$' and H$_5$), 5.14 ppm ($OCH_2O$), 5.18 ppm ($H_{13}$). MS: molecular peak ($M^+$): 690$^+$ PREPARATION 2: 9-[O-[(2-methoxy-ethoxy)-methyl]-oxime] of 6-O-methyl erythromycin.

1.35 g of sodium methylate were added at +5° C. to a solution of 15.2 g de 6-O-methyl erythromycin 9-oxime in 80 ml of tetrahydrofuran and the mixture was stirred for 15 minutes at +5° C. Then, 2.85 ml of (2-methoxy-ethoxy) methyl chloride in solution in 20 ml of tetrahydrofuran were added and the mixture was stirred for 30 minutes at +5° C., then allowed to return to ambient temperature. The tetrahydrofuran was evaporated off under reduced pressure and the residue was taken up in methylene chloride, washed with water, dried and evaporated to dryness. The 16.1 g of residue were chromatographed on silica (eluant: methylene chloride-methanol-ammonium hydroxide 95-5-0.1) to obtain a first fraction of 8.1 g, then a second fraction of 3.56 g of the desired product.

IR Spectrum (CHCl$_3$) OH: 3600 cm$^{-1}$ C=O: 1728 cm$^{-1}$ C=N: 1630 cm$^{-1}$ Mass Spectrum (FAB) (M+H)$^+$: 851$^+$

EXAMPLE 3

3-de[(2,6-dideoxy-3-C-methyl-3-O-methyl-α-L-ribo-hexopyranosyl-oxy]-6-O-methyl-3-oxo erythromycin Step A: 3-O-de(2,6-dideoxy-3-C-methyl-3-O-methyl-α-L-ribo-hexopyranosyl)- 6-O-methyl erythromycin.

380 mg of 6-O-methyl erythromycin were suspended in 3 ml of water and 0.3 ml of 22° Be hydrochloric acid were added. The reaction mixture was stirred for 2 hours and the mixture was adjusted to basic pH (>8) by adding a few drops of ammonium hydroxide at 20° C., and then was diluted with 5 ml of ethyl acetate. The aqueous phase was saturated with sodium chloride, decanted, extracted with ethyl acetate, dried over magnesium sulfate and the solvent was evaporated off. The 350 mg of crude product were chromatographed on silica and eluted with an ethyl acetate-triethylamine (96-4) mixture to obtain 200 mg of the desired product.

IR Spectrum (CHCl$_3$ on Nicolet[OH: 3450 cm$^{-1}$ C=O: 1725, 1689 cm$^{-1}$

Mass Spectrum (FAB) (M+H)$^+$: 590$^+$

Step B: 2'-O-acetyl-3-O-de(2,6-dideoxy-3-C-methyl-3-O-methyl-α-L-ribo-hexopyranosyl)- 6-O-methyl erythromycin.

310 mg of the product of Step A, 80 microliters of acetic anhydride and 90 mg of potassium carbonate were dissolved in 4 ml of acetone with stirring under a nitrogen atmosphere. After 12 hours at ambient temperature, 20 microliters of acetic anhydride and 10 mg of potassium carbonate were added. The mixture was stirred again for 12 hours at ambient temperature and after ice was added, the mixture was stirred, followed by extraction with methylene chloride, drying over magnesium sulfate and the solvent was evaporated off. The product was chromatographed on silica eluting with an ethyl acetate-triethylamine (96-4) mixture to obtain the desired product.

ANALYSIS:

Mass Spectrum (FAB) (M+H)$^+$: 631$^+$

Step C: 3-de[(2,6-dideoxy-3-C-methyl-3-O-methyl-α-L-ribo-hexopyranosyl)-oxy]-6-O-methyl-3-oxo erythromycin.

Step C1: Oxidation 420 mg of the product of Step B, 0.84 ml of dimethylsulfoxide and 0.84 g of 1-[3-(dimethyl-amino)-propyl]-3-ethyl carbodiimide hydrochloride were dissolved in 5 ml of methylene chloride and the solution was stirred for 4 hours at ambient temperature. 4 ml of water were added to the solution and after stirring for 10 minutes, the mixture was taken up in 20 ml of methylene chloride, followed by washing with water, drying over magnesium sulfate and the solvents were evaporated off. The product was chromatographed on silica and eluted with an isopropyl ether-triethylamine (9-1) mixture to obtain 130 mg of the desired product.

Step C2: Hydrolysis

Using the procedure of Step C2 of Example 1, 130 mg of the product of Step C1 were reacted to obtain 100 mg of the desired product after chromatographing on silica (eluant: isopropyl ether-triethylamine (9-1)).

IR: (CHCl$_3$ on Nicolet) OH: 3475 cm$^{-1}$ C=O: 1745, 1714, 1689 cm$^{-1}$

MS: (M+H)$^+$: 588$^+$

NMR: (CDCl$_3$, 300 MHz ppm) 3.86 (H$_2$), 2.6 (H$_4$), 1.35 (6-CH$_3$), 2.7 (6-OCH$_3$), 3.1 (H$_8$), 2.97 (H$_{10}$), 3.91 (H$_{11}$), 1.22 (H$_{12}$), 5.12 (H$_{13}$), 0.86 (H$_{15}$), 4.32 (H$_1$), 3.18 (H'$_2$), 2.46 (H'$_3$), 2.26 (N—CH$_3$), 3.57 (H'$_5$). [α]$_D$=+21° (c=0.5% in CHCl$_3$)

EXAMPLE 4

9-[O-[(2-methoxy-ethoxy)-methyl]-oxime] of 3-de [(2,6-dideoxy-3-C-methyl-3-O-methyl-α-L-ribo-hexopyranosyl)-oxy]-6-O-methyl-3-[(phenylmethoxy)-imino] erythromycin 500 mg of the product of Example 2 were dissolved in 10 ml of ethanol and 172 microliters of triethylamine and 543 mg of 0-benzylhydroxylamine hydrochloride were added. The mixture was refluxed for 4 days and then 172 microliters of triethylamine and 543 mg of 0-benzyl hydroxylamine hydrochloride were added. The mixture was refluxed for a further 3 days and the reaction medium was filtered. The solvents were evaporated off and the residue was taken up in methylene chloride and water. Neutralization was effected with ammonium hydroxide and after decanting, the aqueous phase was extracted with methylene chloride. The combined organic phases were washed with water, dried over magnesium sulfate, filtered and concentrated to dryness to obtain 800 mg of an oil which was chromatographed on silica. Eluting first with ethyl acetate alone, then with an AcOEt/TEA (99-1) mixture yielded 500 mg of a solid which was purified by preparative HPLC. [Eluant: acetonitrile-ammonium acetate 0.2M (4-1)] to obtain 130 mg of the desired product.

NMR: (CDCl$_3$), 300 MHz 0.86 (t) ppm (ethyl CH$_3$), 0.9 to 1.45 (other methyls), 2.27 (s) (N (Me)$_2$) 2.90 (dq) (H$_{10}$,) 2.30 (m) (H$_3$), 3.28 (m) (H$_4$ or H'$_5$, shielded), 4.52 (q) (H$_2$), 2.70 (s) (6-OMe), 3.54 (m) and 3.76 (m) (OCH$_2$CH$_2$O of MEM), 5.13 (OCH$_2$O of MEM and OCH$_2$$^\phi$), 4.00 (wide s) (H$_{11}$), 4.59 (d) (H$_1$'), 3.18 (dd) (H$_2$'), 4.01 (d) (H$_5$), 5.29 (dd) (H$_{13}$), 7.31 (Phenyl).

Mass Spectrum: Molecular peak (M+H)$^+$=796$^+$

IR Spectrum: (CHCl$_3$ on Nicolet) OH: ~3600 cm$^{-1}$+ associated complex C=O: 1730" C=N: ~1636" 1606" Aromatic: 1494"

EXAMPLE 5

9-[O-[(2-methoxy-ethoxy)-methyl]-oxime] of 3-de [(2,6-dideoxy-3-C-methyl-3-O-methyl-α-L-ribo-hexopyranosyl)-oxy]-3-(hydroxyimino)-6-O-methyl erythromycin 110 mg of the product of Example 4 were dissolved in 12.5 ml of ethanol and 52 mg of palladium at 10% on activated charcoal were added. The solution was maintained under hydrogen pressure for 2 days and after filtering and evaporating, the residue was purified by chromatographing on silica and eluting with an isopropyl ether-methanol-triethylamine (90-5-5) mixture to obtain 39 mg of the desired product (1 isomer).

NMR: (CDCl$_3$), 300 MHz 0.87 (t) ppm (ethyl CH$_3$), 0.99 (d) 1.18 (d) 1.26 (d) 1.40 (d) (other methyls), 1.23 (s) (12-Me), 1.36 (s) (6-Me), 2.23 (s) (N(Me)$_2$), 2.90 (dq) (H$_{10}$), ~2.30 (m) (H$_3$'+1 other H), 4.49 (q) (H$_2$), 2.86 (s) (6-OMe), 3.38 (s) (OMe of MEM), 3.54 (m) and 3.76 (m)

(OCH$_2$CH$_2$O of MEM), 5.15 (OCH$_2$O of MEM), 4.56 (d) (H$_1$'), 3.27 (dd) (H$_2$'), 4.05 (wide s) 4.20 (d) (H$_5$ and H$_{11}$), 5.31 (dd) (H$_{13}$), ~3.31; 4.39 (s) ; 1.80 (mobile H's), MS: Molecular peak M$^+$=705$^+$ IR: (CHCl$_3$ on Nicolet) OH: ~3590 cm$^{-1}$+associated C=O: 1725"

EXAMPLE 6

9-[O-[(2-methoxy-ethoxy)-methyl]-oxime] of 3-de (2,6-dideoxy-3-C-methyl-3-O-methyl-α-L-ribo-hexopyranosyl)-oxy]-2-methyl-6-O-methyl-3-oxo erythromycin Step A: 9-[O-[(2-methoxy-ethoxy)-methyl]-oxime] of 2'-O-acetyl-3-de[(2,6-dideoxy-3-C-methyl-3-O-methyl-α-L-ribo-hexopyranosyl)-oxy]-2-methyl-6-O-methyl-3-oxo erythromycin.

0.1 g of the product of example 2, Step B and 17 microliters of methyl iodide were dissolved in 1 ml of methylene chloride and then 0.046 g of the tetrabutylammonium hydrogensulfate, 0.20 ml of water and 0.27 ml of N sodium hydroxide solution were added. The mixture was stirred for 5 hours, followed by extracting with methylene chloride and washing with water. The combined organic phases were dried, filtered and evaporated to dryness under reduced pressure. The residue was taken up in ethyl acetate and filtered. The filtrate was evaporated to dryness to obtain 130 mg of product which was chromatographed on silica and eluted with an ethyl acetate-triethylamine (98-2) mixture to obtain 49 mg of the desired product with a Rf=0.2.

NMR: (CDCl$_3$, 300 MHz)

The disappearance of the proton in position 2 and a modification to the H$_4$ proton was noted. 0.85 ppm (CH$_3$(—CH$_2$)), 0.99–1.28–1.88 ppm (CH$_3$(—CH)), 1.25–1.36–1.50 ppm (CH$_3$(—C)), 2.03 ppm (OAc), 3.30 ppm (dq, J=3 and 7 hz) (H$_4$), 3.4 to 3.8 ppm (OCH$_2$CH$_2$O).

Step B: 9-[O-[(2-methoxy-ethoxy)-methyl]-oxime] of 3-de [(2,6-dideoxy- 3-C-methyl-3-O-methyl-α-L-ribo-hexopyranosyl)-oxy]-2-methyl- 6-O-methyl-3-oxo erythromycin.

0.095 g of the product of Step A were dissolved in 5 ml of methanol and the mixture was stirred for 24 hours at ambient temperature to obtain 95 mg of product which was purified by chromatography on silica eluting with an ethyl acetate-triethylamine mixture (98-2) to obtain 46 mg of the desired product.

NMR: (CDCl$_3$, 300 MHz).

The disappearance of the protons of the "OAc" group was noted. 0.85 ppm (CH$_3$(—CH$_2$)), 0.99–1.18–1.23–1.35 ppm (CH$_3$(—CH)), 1.26–1.32–1.37–1.52 ppm (CH$_3$(—C)), 2.82 ppm (6-OMe), 3.54–3.76 ppm (OCH$_2$CH$_2$O), 3.35–4.33 ppm (mobile H's).

MS: (M+H)$^+$: 705$^+$

EXAMPLE 7

3-de [(2,6-dideoxy-3-C-methyl-3-O-methyl-α-L-ribo-hexopyranosyl]-oxy)-6-O-methyl-3-oxo erythromycin cyclic 11,12-carbonate Step A: 3-O-de[(2,6-dideoxy-3-C-methyl-3-O-methyl-α-L-ribo-hexopyranosyl)- 6-O-methyl erythromycin 2'-acetate cyclic 11, 12 carbonate.

952 microliters of 22° Be hydrochloric acid were added to a suspension of 876 mg of 6-O-methyl erythromycin 2'-acetate 4"-(phenylmethyl carbonate) cyclic 11,12-carbonate (obtained by Baker et al, J. Org Chem., 1988, Vol 53, p. 2340–2345) in 25 ml of methanol and the mixture was stirred for 16 hours at ambient temperature. The methanol was evaporated off and the residue was neutralized with 2N sodium hydroxide. Extraction took place with methylene chloride, followed by drying, filtering and evaporating to dryness. The residue was chromatographed on silica and eluted with ethyl acetate-triethylamine (95-5) to obtain 463 mg of the desired product.

NMR Spectrum: (CDCl$_3$), 300 MHz 0.87 (t) ppm (CH$_3$ of ethyl), 1.28 (s) (6-Me) 0.94 (d) –1.11 (d) –1.19 (d) –1.24 (d) –1.25 (d) (other Me's) 1.49 (s) (12-Me) 2.06 (s) (OAc), 2.26 (s) (N(Me)$_2$), 2.5 to 2.75 (H$_2$, H$_3$', H$_8$), 2.95 (q) (H$_{10}$), 2.92 (s) (6-OMe), 3.49 (m) (H$_5$' and H$_3$), 3.70 (d,J=2.5) (H$_5$), 4.73 (s) (H$_{11}$), 4.58 (s, J=7.5) (H$_1$'), 4.75 (dd) (H$_2$'), 5.13 (dd) (H$_{13}$).

Step B: 3-de[(2,6-dideoxy-3-C-methyl-3-O-methyl-α-L-ribo-hexopyranosyl)-oxy]-6-O-methyl-3-oxo erythromycin cyclic 11,12-carbonate 2'-acetate.

962 microliters of dimethyl sulfoxide and 752 mg of 1-ethyl-3-( 3-dimethylamino-propyl) carbodiimide hydrochloride (EDAC) were added to a solution of 368 mg of the product of Step A and the mixture was stirred for 20 minutes at ambient temperature. 742 mg of pyridinium trifluoroacetate were added and the mixture was stirred for 16 hours. 10 ml of water were added, followed by stirring and extracting with methylene chloride, washing with a solution of sodium bicarbonate, drying, filtering and evaporating to dryness. The residue was chromatographed on silica and eluted with ethyl acetate-triethylamine (98-2) to obtain 278 mg of the desired product which was used as is for the following step.

Step C: 3-de[(2,6-dideoxy-3-C-methyl-3-O-methyl-α-L-ribo-hexopyranosyl)-oxy]-6-O-methyl-3-oxo erythromycin cyclic 11,12-carbonate.

278 mg of the product of Step B dissolved in 20 ml of methanol were stirred for 16 hours at ambient temperature and the solvent was evaporated off. The residue of 245 mg, to which 75 mg were added from a prior preparation was chromatographed on silica to obtain 254 mg of the desired product which was crystallized from ether to obtain 176 mg of the expected product with a specific rotation of [α]$_D$=63° (c=0.45% in CHCl$_3$)

NMR Spectrum: (CDCl$_3$), 400 MHz ppm 2.65 (s) (6-OCH$_3$), 2.68 (m) (H$_8$), 2.97 (q) (H$_{10}$), 3.04 (q) (H$_4$), 3.18 (dd) (H$_2$'), 3.81 (q) (H$_2$), 4.31 (d) (H$_1$'), 4.18 (d) (H$_5$), 4.61 (H$_{11}$).

EXAMPLE 8

(9S) 3-de[(2,6-dideoxy-3-C-methyl-3-O-methyl-α-L-ribo-hexopyranosyl]-oxy)-9-deoxo-6-O-methyl-3-oxo-9-(1-piperidinyl) erythromycin Step A: 9-deoxo-9-imino-6-O-methyl erythromycin.

45.1 ml of 15% titanium chloride were added to a solution of 8.4 g of 6-O-methyl erythromycin 9-oxime (obtained by EP 0,180,415) with 220 ml of methanol and 44 g of ammonium acetate and the mixture was stirred for 3 hours at ambient temperature. The mixture was poured into 500 ml of methylene chloride and 10% solution of potassium carbonate was added, followed by filtering, decanting, washing with water, drying and evaporating to dryness to obtain 7.08 g of the expected product which was used as is for the following step.

Step B: 9-deoxo-9-amino-6-O-methyl erythromycin.

7.0 g of the product of Step A were dissolved in 140 ml of acetic acid and catalytically reduced in the presence of 700 mg of 80% platinum oxide under a hydrogen atmosphere at a pressure of 1400 mbar. Once absorption had finished, filtering took place, followed by washing with methylene chloride and evaporating to dryness. The residue was taken up in methylene chloride, washed with a solution of sodium bicarbonate, dried and evaporated to dryness to obtain 6.71 g of the expected product which was used as is for the following step.

Step C: 9-amino-3-O-de(2,6-dideoxy-3-C-methyl-3-O-methyl-α-L-ribo-hexopyranosyl)- 9-deoxo-6-O-methyl erythromycin.

2 g of the product of Step B, 40 ml of water and 1 ml of 22° Be hydrochloric acid were stirred for 5 hours at ambient temperature and then sodium chloride was added and the pH was brought to 8–9 with ammonium hydroxide. Extraction was effected with methylene chloride and the mixture was evaporated to dryness under reduced pressure. The 2.2 g of residue were chromatographed on silica and eluted with ethyl acetate-methanol-triethylamine (92-5-3) to obtain 1.22 g of the desired product which was used as is for the following step.

Step D: (9S) 3-O-de(2,6-dideoxy-3-C-methyl-3-O-methyl-α-L-ribo-hexopyranosyl)- 9-deoxo-6-O-methyl-9-(1-piperidinyl) erythromycin.

0.28 ml of acetic acid and 0.6 ml of glutaraldehyde at 50% in water were added to a solution of 0.59 g of the product of Step C in 2.8 ml of methanol and then 0.125 g of sodium cyanoborohydride were added. The mixture was stirred for 90 minutes at ambient temperature and was then poured into 90 ml of a 5% aqueous solution of monosodium phosphate. The mixture was extracted with methylene chloride, dried, filtered and evaporated to dryness to obtain 0.7 g of residue which was chromatographed on silica (eluant: ethyl acetate-triethylamine (98-2)) to obtain 328 mg of the desired product.

IR Spectrum: (CHCl$_3$ on Nicolet) OH complex 3490–3390 cm$^{-1}$ C=O 1723 cm$^{-1}$ NMR Spectrum: (CDCl$_3$), 300 MHz 0.85 (t) ppm (ethyl CH$_3$), 1.01 (s) (12-CH$_3$), 1.28 (s) (6-CH$_3$), 2.72 (dq) (H$_2$), 3.84 (dl) (H$_3$), ≅1.54 (m) (H$_4$), ≅3.39 (masked) (H$_5$), 3.10 (s) (6-OMe), 5.02 (dd) (H$_{13}$), 1.47 (m) and 1.89 (m) (ethyl CH$_2$), 3.93 (s) (H$_{11}$), 2.85 to 3.1 (m) (H$_9$ and H$_{10}$), 2.65 (mixture) and 2.86 (mixture) (NCH$_2$') 4.62 (d) (H$_1$'), 3.24 (dd) (H$_2$'), 2.50 (m) (H$_3$'), 1.27 (m) and 1.66 (m) (CH$_2$ in position 4'), 3.53 (m) (H$_5$').

Step E: (9S) 3-O-de(2,6-dideoxy-3-C-methyl-3-O-methyl-α-L-ribo-hexopyranosyl)- 9-deoxo-6-O-methyl-9-(1-piperidinyl) erythromycin 2'-acetate.

242.8 mg of potassium carbonate and 172.7 microliters of acetic anhydride were added to a solution of 160 mg of the product of Step D in 9 ml of acetone and the mixture was stirred for 72 hours at ambient temperature. The reaction medium was poured over ice and extracted with ether, washed with a solution of sodium bicarbonate, then with water, dried and evaporated to dryness to obtain 164 mg of the desired product.

IR Spectrum: CHCl$_3$ on Nicolet) OAc 1743 cm$^{-1}$ lactone 1723 cm$^{-1}$ OH ≅3520 cm$^{-1}$ NMR Spectrum: (CDCl$_3$), 250 MHz 0.84 (t) ppm (ethyl CH$_3$), 1.05 to 1.30 (CH$_3$ of CH$_3$CH), 2.11 (s) (OAc), 3.12 (wide s) (6-OMe), ≅5.01 (H$_3$), 3.94 (wide s) (H$_{11}$), 2.6 to 3.1 (CH$_2$N and H$_2$, H$_9$, H$_{10}$), 4.85 (d) (H$_1$'), 4.65 (dd) (H$_2$'), ≅3.46 (H$_5$').

Step F: (9S) 3-de[(2,6-dideoxy-3-C-methyl-3-O-methyl-α-L-ribo-hexopyranosyl)oxy]-9-deoxo-6-O-methyl-3-oxo-9-(1-piperidinyl) erythromycin 2'-acetate.

Using the procedure of Step B of Example 7, 207 mg of the product of Step E, 489 microliters of dimethyl sulfoxide, 374 mg of [1-ethyl-3-(3-dimethyl-aminopropyl) carbodiimide] (E.D.A.C.) and 374 mg of pyridinium trifluoroacetate were reacted to obtain after chromatographing on silica (eluant isopropyl ether-methanol-triethylamine (95-5-5)), 120 mg of the expected product which was used as is for the following step.

Step G: (9S) 3-de[(2,6-dideoxy-3-C-methyl-3-O-methyl-α-L-ribo-hexopyranosyl)-oxy]-9-deoxo-6-O-methyl-3-oxo-9-(1-piperidinyl) erythromycin.

Using the procedure of Step C of Example 7, 120 mg of the product of Step F were reacted to obtain after chromatographing on silica (eluant isopropyl ether-methanol-triethylamine (95-5-5)) then Microbondapack® C18, eluant: acetonitrile-water (80-20) (with 0.075% trifluoroacetic acid), 70 mg of the desired product with a specific rotation of $\{\alpha\}_D$+ 39° (c=1% in CHCl$_3$)

NMR Spectrum: (CDCl$_3$), 300 MHz 0.88 (t) ppm (ethyl CH$_3$), 1.08 (s) (12-Me), 1.23 (s) (6-Me), 1.01 to 1.28; 1.44 (d) (CH$_3$ of CH$_3$CH), 2.34 (s) (N(Me)$_2$), 2.5 to 2.8 (CH$_2$N, H$_3$, and others), 3.13 (s) (OMe), 3.51 (m) (H$_5$, and H$_2$'), 3.22 (s) (H$_{11}$'), 3.98 (q) (H$_2$), 4.35 (d) (H$_1$'), 4.78 (d) (H$_5$'), 5.05 (dd) (H$_{13}$').

EXAMPLE 9

(9S) 9-amino 3-de[(2,6-dideoxy-3-C-methyl-3-O-methyl-α-L-ribo-hexopyranosyl)-oxy]-9-deoxo-6-O-methyl-3-oxo erythromycin Step A: 3-O-de(2,6-dideoxy-3-C-methyl-3-O-methyl-α-L-ribo-hexopyranosyl)- 9-deoxo-6-O-methyl-9-[[(benzyloxy-carbonyl]-amino]erythromycin 2'(benzyl carbonate).

0.8 ml of benzyl chloroformate were added to a mixture of 1.5 g of the product of Step C of Example 8 with 11 ml of dioxane and 0.88 g of potassium carbonate and the mixture was stirred for 5 hours at ambient temperature. 0.44 g of potassium carbonate and 0.4 g of benzyl chloroformate were added to the mixture which was stirred for 2 hours. The mixture was taken up in methylene chloride, washed with water, dried and evaporated to dryness under vacuum. The 2.5 g of residue were chromatographed on silica (eluant: methylene chloride-methanol-triethylamine (96-3-1)) to obtain 1.71 g of the desired product which was used as is for the following step.

Step B: (9S) 3-de[(2,6-dideoxy-3-C-methyl-3-O-methyl-α-L-ribo-hexopyranosyl)-oxy]-9-deoxo-6-O-methyl-3-oxo-9-[[(benzyloxy)-carbonyl]-amino] erythromycin 2'(benzyl carbonate).

Using the procedure of Step B of Example 7, 2 g of the product of Step A, 1.5 ml of dimethylsulfoxide, 1.8 g of E.D.A.C. and 1.8 g of pyridinium trifluoroacetate were reacted to obtain after chromatographing on silica (eluant: methylene chloride-methanol (97-3)), 757 mg of the desired product which was used as is for the following step.

Step C: (9S) 3-de[(2,6-dideoxy-3-C-methyl-3-O-methyl-α-L-ribo-hexopyranosyl)-oxy]-9-deoxo-6-O-methyl-3-oxo-9-[[(benzyloxy)-carbonyl]-amino] erythromycin.

Using the procedure of Step C of Example 7, 0.75 g of the product of Step B were reacted to obtain after chromatography on silica, 372 mg of the desired product which was used as is for the following step.

Step D: (9S) 9-amino-3-de[(2,6-dideoxy-3-C-methyl-3-O-methyl-α-L-ribo-hexopyranosyl)-oxy)-9-deoxo-6-O-methyl-3-oxo erythromycin.

150 mg of the product of Step C, 6 ml of acetic acid and 150 mg of palladium at 9.5% on activated charcoal were stirred for 24 hours under hydrogen pressure (1.5 bar) and after filtering, washing with ethanol and evaporating to dryness, the residue was taken up in methylene chloride, washed with the 2N sodium hydroxide, then with water, dried and evaporated to dryness. After chromatographing on silica (eluant: chloroform-methanol-ammonium hydroxide(9-1-0.1)), 50 mg of the desired product were obtained.

NMR Spectrum: (CDCl$_3$) ppm 1.88 (H$_8$), 1.94 (H$_{10}$), 2.48 (H$_{3'}$), 2.55 (H$_9$), 3.08 (H$_4$), 3.28 (H$_{2'}$), 3.65 (H$_{11}$), 3.8 (H$_2$), 4.3 (H$_{1'}$), 5.13 (H$_{13}$).

EXAMPLE 10

11,12-dideoxy-3-de[(2,6-dideoxy-3-C-methyl-3-O-methyl-α-L-ribo-hexopyranosyl)-oxy]-6-O-methyl-3-oxo-12,11-]oxycarbonyl-[(4-phenylbutyl)-imino]] erythromycin Step A: 11,12-dideoxy-3-O-de(2,6-dideoxy-3-C-methyl-3-O-methyl-α-L-ribo-hexopyranosyl)- 6-O-methyl-12,11-[oxycarbonyl-[(4-phenylbutyl)-imino]] erythromycin 2'-acetate.

649 mg of 11,12-dideoxy-6-O-methyl-12,11-[oxycarbonyl-[(4-phenylbutyl)-imino]] erythromycin 2'-acetate-4"-(benzyl carbonate) [whose preparation is described infra] were introduced into a solution of 13 ml of methanol and 0.23 ml of concentrated hydrochloric acid and the reaction mixture was stirred for 48 hours at ambient temperature. The methanol was evaporated off under reduced pressure and 10 ml of ethyl acetate were added. After ice-cooling, neutralizing and decanting, the aqueous phase was extracted with ethyl acetate, washed and dried to obtain 626 mg of a product which was chromatographed on silica, eluant: ethyl acetate-methanol (95-5) to obtain 339 mg of the desired product.

IR Spectrum in CHCl$_3$ OH 3618 cm$^{-1}$ 3594 cm$^{-1}$ C=O 1740 cm$^{-1}$ 1711 cm$^{-1}$ C$_6$H$_5$C 1492 cm$^{-1}$ Mass Spectrum of molecular peak 789.6=MH$^+$ NMR spectrum CDCl$_3$ 300 MHz 2.45–2.8 (m) CH$_2$Ph+ H$_2$+H$_8$+H$_3$ax 3.42 (dd) H$_3$ 3.65 (m) CH$_2$N—C=O 4.76 (dd) H$_2$ax 7.11–7.28 aromatics Step B: 11,12-dideoxy-3-de[(2,6-dideoxy-3-C-methyl-3-O-methyl-α-L-ribo-hexopyranosyl)-oxy]-6-O-methyl-12,11-[oxycarbonyl-[(4-phenylbutyl)-imino]] erythromycin 2'-acetate.

A solution of 300 mg of the product of Step A and 2.15 ml of methylene chloride was poured at 21° C. into a suspension of 0.4 ml of DMSO, 1.6 ml of methylene chloride and 438 mg of EDAC and the reaction mixture was stirred at ambient temperature for 30 minutes After cooling down to 15° C., a solution of 438 mg of pyridinium trifluoroacetate in 1.5 ml of methylene chloride was introduced and the mixture was washed with a solution of sodium bicarbonate, then with water, dried and evaporated to dryness to obtain 348 mg of the product which was used as is in the following stage. Rf=0.13.

| NMR CDCl$_3$ ppm | |
| --- | --- |
| 2.07 (s) | \-OCCH$_3$\-<br>‖<br>O |
| 3.00 | H$_4$ |
| 3.89 (q) | H$_2$ |
| 3.66 (m) | \-CH$_2$—N—C\-<br>‖<br>O |
| 7.10 to 7.30 | aromatic H |
| 4.74 (dd) | H$_2'$ |

Step C: 11,12-dideoxy-3-de[(2,6-dideoxy-3-C-methyl-3-O-methyl-α-L-ribo-hexopyranosyl)-oxy]-6-O-methyl-3-oxo-12,11-[oxycarbonyl-[(4-phenylbutyl)-imino]] erythromycin.

278 mg of the product of Step B were suspended in 3 ml of methanol and the reaction mixture was stirred for 60 hours at ambient temperature. After chromatography on silica and eluting with an ethyl acetate-methanol mixture (95-5), the methanol was evaporated off under reduced pressure to obtain 280 mg of product which was chromatographed with a methylene chloride-methanol (9-1) mixture to obtain 133 mg of the desired product.

IR Spectrum OH: 3440 cm$^{-1}$ C=O: 1747 cm$^{-1}$ $^{1711}$ cm$^{-1}$

NMR 2.49 dd H$_3'$ 3.20 dd H$_2'$ 3.10 H$_4$ 3.86 H$_2$

Preparation of the starting product of Example 10.

830 mg of 4-phenyl-butylamine were introduced under an argon atmosphere into a suspension of 1.17 g of 10,11-didehydro-11-deoxy-6-O-methyl-erythromycin 2'-acetate-12-(1H-imidazole-1-carboxylate)-4"-(phenylmethyl-carbonate) [prepared as J. Org. Chem. (1988), Vol. 53, p. 2340–2345], 2.7 ml of methylene cyanide and 0.27 ml of water and the reaction mixture was stirred for 2 hours at 50°. 150 ml of methylene chloride were added and the mixture was cooled in an ice bath. 30 ml of a 0.5M solution of sodium acid phosphate were added, followed by decanting, extracting with methylene chloride, washing, drying and evaporating to dryness. The product was chromatographed on silica, eluant: ethyl acetate-methanol (95-5) to obtain 952 mg of the desired product.

IR Spectrum C=O 1739 cm$^{-1}$ $^{1711}$ cm$^{-1}$ C$_6$H$_5$C 1495 cm$^{-1}$

Ultra-violet spectrum inf: 216 nm E$_1$=103 inf: 259 nm E$_1$=4.5 inf: 266 nm E$_1$=3

Mass spectrum molecular peak=1081.7=MH$^+$

NMR spectrum In CDCl$_3$ at 400 MHz.

| 2.5 to 2.8 | NCH$_2$C$_6$H$_5$H$_8$H$_{3'}$ |
| --- | --- |
| 3.66 | \-CNCH$_2$\-<br>‖<br>O |
| 3.60 | H$_{1'}$ |
| 7.10 to 7.25 | C$_6$H$_5$(CH$_2$)$_4$ |
| 7.35 | C$_6$H$_5$CH$_2$O |

EXAMPLE 11

11,12-dideoxy-3-de[(2,6-dideoxy-3-C-methyl-3-O-methyl-α-L-ribo-hexopyranosyl)-oxy]-6-O-methyl-3-oxo-12,11-[oxycarbonyl-[[2-methyl-benzyl)-imino]-ethyl]-imino]] erythromycin Step A: 11,12-dideoxy-3-O-de[(2,6-dideoxy-3-C-methyl-3-O-methyl-α-L-ribo-hexopyranosyl)-oxy]-6-O-methyl-3-oxo-12,11-[oxycarbonyl-[[2-[methyl-(benzyl)-imino]] erythromycin.

460 mg of the product prepared hereafter (preparation of the starting product of Example 11), 9.2 ml of methanol and 0.23 ml of a solution of concentrated hydrochloric acid were stirred for one hour at ambient temperature, then for 48 hours at ambient temperature. The residue was taken up in water, then in methylene chloride. After adjusting to a basic pH, the mixture was decanted. The aqueous phase was extracted with methylene chloride, washed, dried and evaporated to dryness to obtain 432 mg of product which was chromatographed on silica: eluant ethyl acetate-methanol (9-1) to obtain 312 mg of the desired product.

IR Spectrum: OH: 3618 cm$^{-1}$ 3594 C=O: 1742 cm$^{-1}$ 1709 cm$^{-1}$

| NMR in CDCl$_3$ at 300 MHz | |
|---|---|
| 1.42 (s) | 6Me |
| 1.24 (s) | 12Me |
| 2.20 (s) | CH$_3$—N< |
| 3.48 (d)–3.77 (d) | >N—CH$_2$—C$_6$H$_5$ |
| 3.80 (m)–3.95 (m) | \−C—N—CH$_2$\− ‖ O |
| 3.40 | \−−CH$_2$—N(C$_6$H$_5$)(CH$_3$\−) |
| 4.74 | H$_2$' |

Step B: 11,12-dideoxy-3-de[(2,6-dideoxy-3-C-methyl-3-O-methyl-α-L-ribo-hexopyranosyl)-oxy]-6-O-methyl-3-oxo-12,11-[oxycarbonyl-[2-[methyl-(methyl-phenyl)-amino]-ethyl]-imino]] erythromycin 2'-acetate.

200 mg of the product of Step A dissolved in 1.4 ml of methylene chloride were added to a suspension of 286 mg of EDAC, 0.26 mg of DMSO and 1.2 ml of methylene chloride and the reaction mixture was stirred for 30 minutes at ambient temperature. After cooling to 14° C., a solution of 286 mg of pyridinium trifluoroacetate and 1.3 ml of methylene chloride was introduced at this temperature and the mixture was stirred for 30 minutes at 15° C. and allowed to return to ambient temperature. After treating with sodium bicarbonate, the mixture was diluted with methylene chloride, washed, dried and evaporated to dryness to obtain 350 mg of crude desired product which was purified by chromatographing on silica, eluant: ethyl acetate-methanol (95-5) to obtain 145 mg of the desired product.

UV Spectrum in EtOH max 258 nm ε=400 in EtOH-NaOH 0.1N max 292 nm ε=20100 Presence beta keto ester

| NMR | |
|---|---|
| 2.17 (s) | \−−N—CH$_3$ / C$_6$H$_5$\− |
| 2.25 (s) | \−CH$_3$, CH$_3$\− \ / N \| |
| 3.48 (d)–3.70 (d) | N—CH$_2$Φ |
| 3.80 | H$_2$ |
| 3.87 | \−O—C—N(CH$_2$)\− ‖ O |
| 4.74 (dd) | H$_2$' |
| 7.17 to 7.30 | aromatics |

Step C: 11,12-dideoxy-3-de[(2,6-dideoxy-3-C-methyl-3-O-methyl-α-L-ribo-hexopyranosyl)-oxy]-6-O-methyl-3-oxo-12,11-[oxycarbonyl-[[2-methyl-(benzyl)-amino]-ethyl]-imino] erythromycin.

106 mg of the product of Step B and 6 ml of methanol were stirred for 16 hours at ambient temperature and the methanol was evaporated off to obtain 106 mg of product which was chromatographed on silica, eluant: ethyl acetate-triethylamine (95- 5) to obtain 55 mg of the desired product.

| NMR: | |
|---|---|
| 1.34 (s) | 12Me |
| 1.48 (s) | 6Me |
| 2.18 (s) | \−N⌢Φ\− \| CH$_3$ |
| 2.27 (s) | \−N(CH$_3$\−)(CH$_3$) |
| 3.00 to 3.24 | H$_2$' and H$_4$ |
| 3.57 (s) | H$_{11}$ |
| 4.23 (d) and 4.28 (d) | H$_1$', H$_5$ |
| 2.48 | H$_3$', H$_8$ and CH$_2$Φ |

Preparation of the starting product of Example 11

11,12-dideoxy-6-O-methyl-12,11-[oxycarbonyl-[[2-[methyl-(benzyl)-amino]-ethyl]-imino]] erythromycin.

Step A: 11,12-dideoxy-6-O-methyl-12,11-[oxycarbonyl-[[2-[methyl-(benzyl)-amino]-ethyl]-imino]] erythromycin.

1.1 g of 10,11-didehydro-11-deoxy-6-O-methyl-erythromycin 2'-acetate- 12-(1H-imidazole-1-carboxylate)-4"-(benzyl carbonate) were introduced into a mixture of 2.7 ml of methyl cyanide and 0.27 ml of water and 1.8 ml of N-benzylethylenediamine were introduced. The reaction mixture was stirred at 50° C. for 5 hours and then was diluted with methylene chloride and cooled down in an ice bath. 30 ml of a 0.5M solution of monosodium phosphate were added followed by decanting, extracting with methylene chloride, washing, drying and evaporating to dryness to obtain 1.6 g of product which was purified by chromatographing on silica eluant ethyl acetate-methanol (98-2) to obtain 800 mg of the desired product.

Infra-red spectrum C=O 1739 cm$^{-1}$ 1710 cm$^{-1}$ C$_6$H$_5$ 1494 cm$^{-1}$

Mass spectrum Molecular peak=1082=MH$^+$

NMR Spectrum In CDCl$_3$ at 300 MHz 3.07 (q) H$_{10}$ 3.34 (s) 3"OMe 3.61 (s) H$_{11}$ 3.83 (m) CH$_2$N—C=O and N—CH$_2$Ph 7.15 to 7.35 N—CH$_2$Ph aromatics Step B: 11,12-dideoxy-6-O-methyl-12,11-[oxycarbonyl-[[2-[methyl-(benzyl)-amino]-ethyl]-imino]] erythromycin.

50 ml of a solution of 37% formaldehyde in formic acid were added to a solution of 13 ml of methylene chloride and 0.60 g of the product of Step A and the reaction mixture was stirred for 4 hours at ambient temperature, then at 70° C. for 7 hours. After diluting with methylene chloride, water was added and the mixture was neutralized with sodium bicarbonate, followed by decanting, washing, drying and evaporating to dryness. After chromatography on silica: eluant ethyl acetate-methanol (95-), 480 mg of the desired product were obtained.

IR Spectrum: C=O 1737 cm$^{-1}$ 1708 cm$^{-1}$ C$_6$H$_5$ 1494 cm$^{-1}$ MS: MH$^+$=1096.9$^+$ NMR spectrum: 1.12 (s) 12 Me 1.40 (s) 6 Me 2.19 CH$_3$—N<2.96 (s) 6 OMe 3.62 (sl) H$_{11}$ 4.30 (m) H$_5$" ax 4.73 (dd) H$_2$" ax 7.15 to 7.39 aromatics 2.87 H$_2$

EXAMPLE 12

9-[O-(2-bromoethyl) oxime of 3-de[(2,6-dideoxy-3-C-methyl-3-O-methyl-α-L-ribo-hexopyranosyl)-oxy]-6-O-methyl-3-oxo erythromycin 880 mg, then 440 mg of 2-bromoethyloxyamine hydrobromide were added, after 24 hours of stirring at ambient temperature to 4.18 g of the product of Example 3 in 20 ml of methanol while maintaining the pH at 3. After another 18 hours of stirring, 30 ml of water were added, the crystals were separated, washed with water and dried at 60° C. to obtain 1.2 g of (9R) 9-deoxo-12-deoxy-3-de(2,6-dideoxy-3-C-methyl-3-O-methyl-α-L-ribo-hexopyranosyl)-oxy]-9, 12-epoxy- 9-methoxy erythromycin melting at 188°–190° C. in 10 ml of water. Concentrated ammonium hydroxide was added until the pH was 11–12. Extraction took place with ethyl acetate, followed by concentration under reduced pressure to obtain 1.0 g of the expected product melting at 150°–152° C.

NMR spectrum (ppm) $CDCl_3$: 0.86 (t) ethyl $CH_3$ 1.23 (s) 12-Me 1.40 (s) 6-Me 2.26 (s) $N(Me)_2$ 2.45 (m) $H_3$ 2.60 (p1) $H_{10}$ 2.76 (s) 6-OMe 3.13 (m) $H_4$ 3.18 (dd) $H_{2'}$ 3.52 (m) $CH_2Br$ 3.55 (m) $H'_5$ 3.70 (m) $H_8E$ isom. 3.86 (q) $H_2$ 3.90 (d) $H_{11}$ 4.18 to 4.35 $H'_1$, $H_5$ and $NOCH_2$+mobile 1H 5.17 (dd) $H_{13}$ 3.26 (s) 3.45 mobile H's.

EXAMPLE 13

(E) 9-O-[2-[[2-(1-pyrrolidinyl-ethyl]-amino]-ethyl]-oxime of 3-de [(2,6-dideoxy-3-C-methyl-3-O-methyl-α-L-ribo-hexopyranosyl)-oxy]-6-O-methyl-3-oxo erythromycin 0.3 g of the product of Example 12 and 3 ml of N-aminoethyl pyrrolidine were stirred for 72 hours at ambient temperature and then 5 ml of ethanol were added. The mixture was stirred for a further 24 hours, followed by evaporating under reduced pressure. The 0.35 g of dry extract were chromatographed on silica (eluant: ethyl acetate-methanol-triethylamine 90-8-2) to obtain 0.204 g of the desired product.

| NMR spectrum (ppm) 300 MHz $CDCl_3$: | |
|---|---|
| 0.86 | $CH_3-CH_2$ |
| 0.98 | 8-$CH_3$ |
| 1.22 | 12-$CH_3$ |
| 1.38 | 6-$CH_3$ |
| 1.75–2.49 | The $CH_2$'s of the pyrrolidinyl |
| 2.26 | $-N-(CH_3)_2$ |
| 2.4 to 2.6 ⎤ 2.74 ⎦ | $HN-CH_2-CH_2-N$ 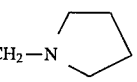 |
| 2.8 to 3 ⎤ 4.0 to 4.2 ⎦ | $O-\underline{CH_2}-\underline{CH_2}-NH$ |
| 3.19 | $H'_2$ |
| 3.86 | $H_2$ |
| 5.17 | $H_{13}$ |

Using the procedure of Example 12, the product of Example 3 and the appropriate hydroxylamine derivative in the form of the hydrochoride were reacted to obtain the products of the following examples.

EXAMPLE 14

(E) 9-O-[(2-pyridinyl)-methyl] oxime of 3-de[(2,6-dideoxy- 3-C-methyl-3-O-methyl-α-L-ribo-hexopyranosyl)-oxy]-6-O-methyl- 3-oxo erythromycin melting at 167°–169° C.

EXAMPLE 15

(E) 9-O-[(3,5-dimethyl-4-isoxazolyl)-methyl] oxime of 3-de[(2,6-dideoxy-3-C-methyl-3-O-methyl-α-L-ribo-hexopyranosyl)-oxy]-6-O-methyl-3-oxo erythromycin melting at 222°–224° C.

EXAMPLE 16

(E) 9-O-[(4-nitrophenyl)-methyl] oxime of 3-de[(2,6-dideoxy- 3- C-methyl-3-O-methyl-α-L-ribo-hexopyranosyl)-oxy]-6-O-methyl- 3-oxo erythromycin with a Rf=0.40 ($CH_2Cl_2$-MeOH-9-1).

EXAMPLE 17

(E) 9-oxime of 3-de[(2,6-dideoxy-3-C-methyl-3-O-methyl-α-L-ribo-hexopyranosyl)-oxy]-6-O-methyl-3-oxo erythromycin melting at 268°–270° C.

Using the procedure of Example 13, the bromine derivative of Example 12 and the appropriate amine reagents were reacted to obtain the products of the following examples.

EXAMPLE 18

9-O-[2-(diethylamino)-ethyl]-oxime of 3-de[(2,6-dideoxy- 3-C-methyl-3-O-methyl-α-L-ribo-hexopyranosyl)-oxy]-6-O-methyl- 3-oxo erythromycin melting at 158°–160° C. and with a specific rotation of $[\alpha]_D$=+2.5° (c=0.5% in $CHCl_3$).

EXAMPLE 19

9-O-[2-(1-pyrrolidinyl)-ethyl]-oxime of 3-de[(2,6-dideoxy- 3-C-methyl-3-O-methyl-α-L-ribo-hexopyranosyl)-oxy]-6-O-methyl- 3-oxo erythromycin melting at 210°–212° C. and with a specific rotation of $[\alpha]_D$=+8.5° (c=0.85% in $CHCl_3$).

EXAMPLE 20

9-O-[2-(1-azetidinyl)-ethyl]-oxime of 3-de[(2,6-dideoxy-3-C-methyl-3-O-methyl-α-L-ribo-hexopyranosyl)-oxy]-6-O-methyl- 3-oxo erythromycin with a Rf=0.37 (AcOEt-MeOH-TEA 90-5-5).

EXAMPLE 21

9-O-[2-(4-morpholinyl)-ethyl] oxime of 3-de[(2,6-dideoxy- 3-C-methyl-3-O-methyl-α-L-ribo-hexopyranosyl)-oxy]-6-O-methyl- 3-oxo erythromycin melting at 198°–200° C. and with a specific rotation of $[\alpha]_D$=+5 to +8° (c=0.85% in $CHCl_3$).

EXAMPLE 22

9-O-[2-(1-piperidinyl)-ethyl] oxime of 3-de[(2,6-dideoxy- 3-C-methyl-3-O-methyl-α-L-ribo-hexopyranosyl)-oxy]-6-O-methyl- 3-oxo erythromycin melting at 194°–196° C. and with a specific rotation of $[\alpha]_D$=+10° (c=0.6% in $CHCl_3$).

EXAMPLE 23

(E) 9-O-[2-(propylamino)-ethyl] oxime of 3-de[(2,6-dideoxy- 3-C-methyl-3-O-methyl-α-L-ribo-hexopyranosyl)-oxy]-6-O-methyl- 3-oxo erythromycin with a Rf=0.34 (AcOEt-TEA 95-5).

EXAMPLE 24

(E) 9-O-[2-(dimethylamino)-ethyl]-amino]-ethyl]oxime of 3-de [(2,6-dideoxy-3-C-methyl-3-O-methyl-α-L-ribo-hexopyranosyl)-oxy]-6-O-methyl-3-oxo erythromycin with a Rf=0.17 (AcOEt-MeOH-TEA 80-10-10).

EXAMPLE 25

(E) 9-O-[2-(4-methyl-1-piperazinyl)-ethyl]-oxime of 3-de [(2,6-dideoxy-3-C-methyl-3-O-methyl-α-L-ribo-hexopyranosyl)-oxy]-6-O-methyl-3-oxo erythromycin melting at 160°–162° C. and with a specific rotation of $[\alpha]_D=-3°$ (c=0.4% in $CHCl_3$).

EXAMPLE 26

(E)9-O-[2-[[3-dimethylamino)-propyl]-amino]-ethyl] oxime of 3-de [(2,6-dideoxy-3-C-methyl-3-O-methyl-α-L-ribo-hexopyranosyl)-oxy]-6-O-methyl-3-oxo erythromycin with a specific rotation of $[\alpha]_D=+6°$ (c=1% in $CHCl_3$).

EXAMPLE 27

(E) 9-O-[2-[[2-(1-piperidinyl)ethyl]-amino]-ethyl] oxime of 3-de [(2,6-dideoxy-3-C-methyl-3-O-methyl-α-L-ribo-hexopyranosyl)-oxy]-6-O-methyl-3-oxo erythromycin with a specific rotation of $[\alpha]_D=+4°$ (c=0.7% in $CHCl_3$).

EXAMPLE 28

(E) 9-O-[2-[(1-methylethyl)-amino]-ethyl] oxime of 3-de [(2,6-dideoxy-3-C-methyl-3-O-methyl-α-L-ribo-hexopyranosyl)-oxy]-6-O-methyl-3-oxo erythromycin melting at 188°–190° C. and with a specific rotation of $[\alpha]_D=+7°$ (c=1% in $CHCl_3$).

EXAMPLE 29

(E) 9-O-[2-(hexahydro-1H-azepin-1-yl)-ethyl] oxime of 3-de[(2,6-dideoxy-3-C-methyl-3-O-methyl-α-L-ribo-hexopyranosyl)-oxy]-6-O-methyl-3-oxo erythromycin melting at 206°–208° C. and with a specific rotation of $[\alpha]_D=+1.2°$ (c=0.85% in MeOH).

EXAMPLE 30

(E) 9-O-(2-aminoethyl) oxime of 3-de[(2,6-dideoxy-3-C-methyl- 3-O-methyl-α-L-ribo-hexopyranosyl)-oxy]-6-O-methyl-3-oxo erythromycin melting at 190°–192° C.

EXAMPLE 31

(E) 9-O-[2-[(2-propynyl)-amino]-ethyl] oxime of 3-de[(2, 6-dideoxy-3-C-methyl-3-O-methyl-α-L-ribo-hexopyranosyl)-oxy]- 6-O-methyl-3-oxo erythromycin melting at 152°–154° C.

EXAMPLE 32

(E) 9-O-[2-[(phenylmethyl)-amino]-ethyl] oxime of 3-de [(2,6-dideoxy-3-C-methyl-3-O-methyl-α-L-ribo-hexopyranosyl)-oxy]- 6-O-methyl-3-oxo erythromycin melting at 200 then 222°–224° C. and using a specific rotation of $[\alpha]_D=+2°$ (c=1% in MeOH).

EXAMPLE 33

(E) 9-O-[2-[methyl-(phenylmethyl)-amino]-ethyl]oxime of 3-de[(2,6-dideoxy-3-C-methyl-3-O-methyl-α-L-ribo-hexopyranosyl)-oxy]-6-O-methyl-3-oxo erythromycin melting at 130°–135° C. and having a specific rotation of $[\alpha]_D=+15°$ (c=0.9% in MeOH).

EXAMPLE 34

(E)9-O-[2-[[3(diethylamino)-propyl]-methyl-amino]-ethyl] oxime of 3-de[(2,6-dideoxy-3-C-methyl-3-O-methyl-α-L-ribo-hexopyranosyl)-oxy]-6-O-methyl-3-oxo erythromycin with a Rf=0.2 ($CH_2Cl_2$-MeOH-$NH_4OH$ 90-10-1).

EXAMPLE 35

(3S) 9-O-[2-(diethylamino)-ethyl] oxime of 3-O-de[(2,6-dideoxy-3-C-methyl-3-O-methyl-α-L-ribo-hexopyranosyl)-oxy]-6-O-methyl-3-oxo erythromycin.

A solution of 0.59 g of the product of Step A of Example 3 and 0.27 g of N,N-dimethylaminoethoxyamine hydrochloride in 12 ml of methanol was refluxed for 4 hours and the solution was taken up in aqueous ethanol and brought to pH=8–9 with ammonium hydroxide, followed by decanting, washing, drying, filtering and evaporating to dryness under reduced pressure. The 0.76 g of residue were chromatographed on silica (eluant: ethyl acetate-triethylamine 95-5) to obtain 158 mg of the expected product which after crystallization from hexane melted at 156° C.

NMR spectrum 300 MHz ($CDCl_3$): 0.87 (t) ethyl $CH_3$ 1.33–1.41 (s) 6 and 12 methyl 2.72 (d, q) $H_2$ 3.48 (d, J=10.5Hz) $H_3$ ~3.72 (d, J=1.5Hz) $H_5$ 4.32 (d, d) $H_{13}$ 1.84 (d, J=1Hz) 10 methyl 5.77 $H_{11}$ 4.21 $OCH_2$ 2.66 $CH_2N$ 4.39 (d) $H'_1$ 3.25 (dd) $H'_2$ 2.48 (m) $H'_3$

EXAMPLE 36

(E) 9-O-[2-(dimethylamino)-ethyl] oxime of 3-de[(2,6-dideoxy-3-C-methyl-3-O-methyl-α-L-ribo-hexopyranosyl)-oxy]-11-deoxy-10,11-didehydro-6-O-methyl-3-oxo erythromycin Step A: (3S) 9-O-[2-(dimethylamino)-ethyl] oxime of 3-O-de[(2,6-dideoxy- 3-C-methyl-3-O-methyl-α-L-ribo-hexopyranosyl)-oxy]-6-O-methyl- 3-oxo erythromycin acetate.

228 mg of the product of Example 35, 96 mg of potassium carbonate and 0.05 ml of acetic anhydride in 4 ml of acetone were stirred for 24 hours at ambient temperature after which a further 19 mg of potassium carbonate and 0.010 ml of acetic anhydride were added. The mixture was stirred for 4 hours and was poured onto ice and the pH was adjusted to 8–9 with ammonium hydroxide. Extraction took place with methylene chloride, followed by drying, filtering and evaporating to dryness under reduced pressure to obtain 250 mg of product which was chromatographed on silica (eluant: ethyl acetate-triethylamine 95-5) to obtain 175 mg of the desired product.

NMR spectrum 300 MHz ($CDCl_3$) 0.86 (t) 15 methyl 0.90 (d) 6 methyl 1.25–1.40 6 and 12 methyl 1.83 (d, J=1 Hz) 10 $CH_3$ 2.06 (s) OAC 2.73 $H_2$ 3.41 (d, J=10Hz) $H_3$ 4.91 (dd) $H_{13}$ 5.74 (d, J=1Hz) $H_{11}$ 4.18 (t) $OCH_2N$ 2.66 $CH_2N$ 4.60 (d) $H'_1$ 4.77 (dd) $H'_2$ Step B: (E) 9-O-[2-(dimethylamino)-ethyl] oxime of 3-de [(2,6-dideoxy- 3-C-methyl-3-O-methyl-α-L-ribo-hexopyranosyl)-oxy]-11-deoxy- 10,11-didehydro-6-O-methyl-3-oxo erythromycin.

160 mg of the product of Step A dissolved in 2 ml of methylene chloride were added to a solution of 240 microliters of dimethylsulfoxide and 240 mg of 1-ethyl-3-(3-dimethylaminopropyl) carbodiimide (EDAC) in 2 ml of methylene chloride and the mixture was stirred for 30 minutes at ambient temperature, followed by cooling to 15° C. While maintaining the said temperature, 260 mg of pyridinium trifluoroacetate in solution in 2 ml of methylene chloride were added and the mixture was stirred for 1 hour at 15° C. 5 ml of water were added and the pH was adjusted to 8–9 with ammonium hydroxide. The mixture was extracted with methylene chloride and the organic phase was washed with water, dried, filtered, evaporated to dryness under reduced pressure, taken up in 10 ml of methanol, stirred for 16 hours and evaporated to dryness under reduced pressure. The 0.3 g of dry residue are chromatographed on silica (eluant: ethyl acetate-triethylamine 95-5) to obtain 62 mg of the desired product.

NMR spectrum 300 MHz (CDCl$_3$) 0.86 (t) 15 CH$_3$ 1.77 and 1.85 10 CH$_3$ 3.89 H$_2$ 4.91 (dd) H$_{13}$ 5.66 and 5.76 H$_{11}$ 4.10 to 4.30 OCH$_2$ 2.65 CH$_2$N 3.20 (dd) H'$_2$ 2.26 and 2.27–2.30 N(CH$_3$)$_2$

EXAMPLE 37

(E) 9-O-(3-piperidinyl) oxime of 3-de[(2,6-dideoxy-3-C-methyl-3-O-methyl-α-L-ribo-hexopyranosyl)-oxy]-6-O-methyl-3-oxo erythromycin a) A solution of 0.6 g of the product of Example 3 and 0.86 g of the product of the preparation below in 12 ml of methanol were heated to 65° C. for 6 hours and the solvent was evaporated off. The residue was taken up in 10 ml of methylene chloride and 10 ml of water were added and the pH was adjusted to 8 with ammonium hydroxide. After decanting, washing with salt water, drying and evaporating to dryness under reduced pressure, the residue was chromatographed on silica (eluant: ethyl acetate-triethylamine 98-2) to obtain 550 mg of the intermediate benzyloxycarbonyl compound.

b) Hydrogenolysis

A solution of 250 mg of the product above in 10 ml of methanol and 100 mg of palladium on activated charcoal was stirred for 12 hours at ambient temperature and under hydrogen pressure of 1.5 bar. After filtering and washing with methanol, the filtrate was evaporated to dryness under reduced pressure. The 200 mg of residue were chromatographed on silica (eluant: chloroform-methanol-ammonium hydroxide 92-8-0.5) to obtain 160 mg of the desired product.

NMR spectrum 300 MHz (CDCl$_3$) 0.86 ethyl CH$_3$ 1.39 (s, d) 6 CH$_3$ 2.26 (s) N(CH$_3$)$_2$ 2.58 H$_{10}$ 2.67–3.16 — CH$_2$—NH—CH$_2$—3.58 H'$_5$ 3.70 H$_8$ 3.87 H$_3$ Preparation of Example 37

O-[1-(benzyloxy-carbonyl)-piperidin-3-yl ] hydroxylamine hydrochloride

Step A: 1-benzyoxycarbonyl 3-hydroxypiperidine. 7.7 ml of benzyl chloroformate in solution in 10 ml of dioxane and 8.2 g of potassium carbonate were added dropwise at 0° C. to a solution of 5 g of 3-hydroxypiperidine in 50 ml of dioxane and the mixture was stirred for 2 hours at ambient temperature. Another 5 g of potassium carbonate, 20 ml of water and 3 ml of benzyl chloroformate in solution in 10 ml of dioxane were added and the mixture was stirred for 1 hour at ambient temperature and concentrated under reduced pressure. The mixture was taken up in 10 ml of water, extracted with ether, dried and concentrated under reduced pressure. After chromatographing on silica (eluant: ethyl acetate-hexane 1-1), 10.8 g of the desired product were obtained.

IR Spectrum (CHCl$_3$) OH 3612 cm$^{-1}$ C=O 1693 cm$^{-1}$ aromatics 1498 cm$^{-1}$ Step B: N-[[1(benzyloxycarbonyl)-piperidin-3-yl]-oxy]-phthalimide.

10.05 g of diethylazodicarboxylate were added at 25° C. over 30 minutes to a solution of 10.8 g of the product of Step A, 8.24 g of N-hydroxyphthalimide and 13.25 g of triphenylphosphine in 225 ml of tetrahydrofuran and the mixture was stirred for 4 hours. Then, the solvent was evaporated under reduced pressure and the residue was chromatographed on silica (eluant: ethyl acetate-hexane 1-1) to obtain 13 g of the expected product in the form of 2 diastereoisomers.

IR Spectrum (CHCl$_3$) CO phthalimide 1790, 1732 cm$^{-1}$ CO carbobenzyloxy 1693 cm$^{-1}$ Step C: O-[1-(benzyloxycarbonyl)-piperidin-3-yl] hydroxylamine hydrochloride.

A solution of 11.9 g of the product of Step B and 1.46 ml of hydrazine hydrate in 60 ml of ethanol was stirred for 1 hour at 60° C. and the insoluble part was filtered off, followed by washing with ether. The filtrate was evaporated to dryness under reduced pressure and the residue was chromatographed on silica (eluant:ethyl acetate-hexane 4-6) to obtain 6 g of the expected product in the form of the base.

Preparation of the Hydrochloride

The product was dissolved in an ether-methanol mixture and the solution was treated with hydrochloric ether. After separating, washing with ether and drying, 6.32 g of the expected hydrochloride were obtained.

IR Spectrum CHCl$_3$ ONH$_2$ 3330, 1586 cm$^{-1}$ CO 1688 cm$^{-1}$ phenyl 1498 cm$^{-1}$ NMR spectrum 250 MHz (CDCl$_3$) 1.42–1.74 H$_4$—H$_5$ 3.10–4.9 H$_2$—H$_3$ 5.13 CH$_2$—Bz 5.23 NH$_2$ 7.36 benzyl

EXAMPLE 38

9-O-[2-[(2-methoxyethyl)-amino]-ethyl] oxime of 3-de[(2,6-dideoxy-3-C-methyl-3-O-methyl-α-L-ribo-hexopyranosyl)-oxy]-6-O-methyl-3-oxo erythromycin.

Step A: 9-O-[2-(bromo)-ethyl] oxime of 3-O-de(2,6-dideoxy-3-C-methyl- 3-0-methyl-α-L-ribo-hexopyranosyl)-oxy]-6-O-methyl erythromycin.

Using the procedure of Example 12, the bromine reagent was reacted with 3-O-de(2,6-dideoxy-3-C-methyl-3-O-methyl-α-L-ribo-hexopyranosyl)-oxy]-6-O-methyl erythromycin to obtain the expected product.

Step B: 0.72 mg of the product of Step A in 3 ml of 2-methoxyethylamine were stirred for 20 hours at ambient temperature and the solvent was evaporated off under reduced pressure. The residue was chromatographed on silica (eluant: ethyl acetate-triethylamine-methanol 9-0.5-0.5) to obtain 730 mg of the expected product which was crystallized from ether.

Step C: 2'-O-(benzylcarbonate) of 9-O-[2-[(benzyloxy-carbonyl)-( 2-methoxyethyl )-amino]-ethyl] oxime of 3-O-de(2,6-dideoxy-3-C-methyl- 3-O-methyl-α-L-ribo-hexopyranosyl)-oxy]-6-O-methyl erythromycin.

0.44 ml of benzyl chloroformate dissolved in 5 ml of dioxane were added dropwise to a mixture of 620 mg of the product of Step B and 490 mg of potassium carbonate in 10 ml of dioxane and after 3 hours of stirring at ambient temperature, 0.4 ml of the chloroformate and 500 mg of additional potassium carbonate were added. The mixture was stirred at ambient temperature for 20 hours and 3 ml of water were then added. The mixture was stirred for 30 minutes, followed by extraction with ethyl acetate, drying and the solvent was evaporated off. After chromatographing on silica (eluant: ethyl acetate), 616 mg of the expected product were obtained with a Rf=0.27.

Step D: 2'-O-(benzylcarbonate) of 9-O-[2(benzyloxy-carbonyl)-(2-methoxyethyl)-amino]-ethyl] oxime of 3-O-de[(2, 6-dideoxy-3-C-methyl- 3-O-methyl-α-L-ribo-hexopyranosyl)-oxy]-6-O-methyl-3-oxo erythromycin.

724 mg of 1-ethyl 3-(3-dimethylaminopropyl) carbodiimide (EDAC) were added to 0.670 ml of dimethylsulfoxide in 4 ml of methylene chloride and 616 mg of the product of Step C in solution in 4 ml of methylene chloride were added. The mixture was stirred for 15 minutes while maintaining the temperature at about 16° C. and 724 mg of pyridinium trifluoroacetate dissolved in 5 ml of methylene chloride were added dropwise. After 3 hours of stirring, 10 ml of methylene chloride and 10 ml of water were added, the mixture was alkalized to pH=8 with ammonium hydroxide, followed by decanting, washing with a saturated aqueous solution of sodium chloride, drying and evaporating the solvent. After chromatographing on silica (eluant: ethyl acetate), 369 mg of the expected product with a Rf=0.28 were obtained.

Step E: 9-O-[2-[(2-methoxyethyl)-amino]-ethyl] oxime of 3-de[(2,6-dideoxy-3-C-methyl-3-O-methyl-α-L-ribo-hexopyranosyl)-oxy]- 6-O-methyl-3-oxo erythromycin.

369 mg of the product of Step D in 10 ml of methanol were hydrogenated at 1.5 bar in the presence of 100 mg of palladium at 9.5% on activated charcoal and the reaction medium was stirred for 20 hours, followed by filtering and washing with methanol. The solvent was evaporated off and the residue was chromatographed on silica to obtain 200 mg of the expected product with a Rf=0.23.

EXAMPLE 39

(E) 9-O-[2-[(3-(diethylamino)-propyl]-methyl-amino]-ethyl] oxime of 3-de(2,6-dideoxy-3-C-methyl-3-O-methyl-α-L-ribo-hexopyranosyl)-oxy]- 6-O-methyl-3-oxo erythromycin 7.5 microliters of formic acid and 14.8 microliters of formaldehyde were added to 100 mg of (E) 9-O-[2-[(3-(dieoxy-3-C-methyl- 3-O-methyl-α-L-ribo-hexopyranosyl)-oxy]-6-O-methyl-3-oxo erythromycin of Example 34 in solution in 6 ml of chloroform and the mixture was stirred for 1 hour at ambient temperature, then refluxed for 3 hours and allowed to return to ambient temperature. 10 ml of water were added and the reaction medium was alkalized to the pH of 9 with sodium hydroxide. The mixture was extracted with aqueous methylene chloride and the organic phase was dried. The solvent was eliminated under reduced pressure to obtain 96 mg of crude product which was chromatographed on silica (eluant: ethyl acetate-triethylamine 95-5). The residue was taken up in methylene chloride, filtered and the solvent was evaporated off to obtain 69 mg of the expected product.

NMR spectrum (ppm) 1.02 (t) 2.52 (q) the NCH$_2$CH$_3$'s 2.35 to 2.75 the NCH$_2$CH$_2$ (6H)'s Using the procedure of Example 39, the products of Examples 40 to 43 were prepared using the products of Examples 23, 24, 26, and 13 respectively as starting materials.

EXAMPLE 40

(E) 9-O-[2-(methylpropylamino)-ethyl] oxime of 3-de( 2,6-dideoxy-3-C-methyl-3-O-methyl-α-L-ribo-hexopyranosyl)-oxy]- 6-O-methyl-3-oxo erythromycin with a Rf=0.39 (AcOEt-TEA 96-4).

EXAMPLE 41

(E) 9-O-[2-[[2-(dimethylamino)-ethyl] methylamino]-ethyl] oxime of 3-de(2,6-dideoxy-3-C-methyl-3-O-methyl-α-L-ribo-hexopyranosyl)-oxy]-6-O-methyl-3-oxo erythromycin with a Rf=0.25 (Ether iso-MeOH-TEA 80-10-10).

EXAMPLE 42

(E) 9-O-[2-[[3-(dimethylamino)-propyl]-methyl-amino]-ethyl] oxime of 3-de[(2,6-dideoxy-3-C-methyl-3-O-methyl-α-L-ribo-hexopyranosyl)-oxy]-6-O-methyl-3-oxo erythromycin with a Rf=0.30 (CH$_2$Cl$_2$-MeOH-TEA 94-3-3).

EXAMPLE 43

(E) 9-O-[2-[[2-(1 pyrrolidinyl)-ethyl]-methylamino]-ethyl]-oxime of 3-de[(2,6-dideoxy-3-C-methyl-3-O-methyl-α-L-ribo-hexopyranosyl)oxy]-6-O-methyl-3-oxo erythromycin. Rf=0,2 (AcOEt-MeOH-TEA 92-5-3).

EXAMPLE 44

9-O-((2-methoxyethoxy)methyl)oxime of 3-deoxy-2,3 didehydro-3-O-de(2,6-dideoxy-3-C-methyl-3-O-methyl-α-L-ribo-hexopyranosyl)- 6-O-methyl-erythromycin with a specific rotation of [α]$_D$=-32° (c=1% in CHCl$_3$).

EXAMPLE 45

9-O-((2-methyl-4-thiazolyl)methyl)oxime de-3-de(2,6-dideoxy- 3-C-methyl-3-O-methyl-α-L-ribo-hexopyranosyl)-6-O-methyl-3-oxo-erythromycin melting at 116°–118° C.

EXAMPLE 46

9-O-((2-methoxyethoxy)methyl)oxime of -3-O-de(2,6-dideoxy- 3-C-methyl-α-L-ribo-hexopyranosyl)-3-O-phenyl-aminocarbonyl)-erythromycin with a specific rotation of [α]$_D$=-18.5° (c=1% in CHCl$_3$).

EXAMPLE 47

3-de(2,6-dideoxy-3-C-methyl-3-O-methyl-α-L-ribo-hexopyranosyl)oxy- 6-O-methyl-3-oxo-erythromycin.

EXAMPLE 48

(E) 9-O-(2-(((tetrahydro-2-furanyl)methyl)ethyl)oxime of 3-de(2,6-dideoxy-3-C-methyl-3-O-methyl-α-L-ribo-hexopyranosyl)-oxy)-6-O-methyl-3-oxo-erythromycin melting at 129°–131° C.

EXAMPLE 49

(E) 9-O-(2-((2-propenyl)amino)de-3-de(2,6-dideoxy-3-C-methyl- 3-O-methyl-α-L-ribo-hexopyranosyl)-oxy)-6-O-methyl-3-oxo-erythromycin melting at 174°–176° C.

EXAMPLE 50

(Z) 9-oxime of 3-de(2,6-dideoxy-3-C-methyl-3-O-methyl-α-L-ribo-hexopyranosyl)-oxy)- 6-O-methyl-3-oxo erythromycin melting at 228°– 230° C.

EXAMPLE 51

(2R) (E)-(2-amino-3-methoxy-3-oxo-propyl) oxime of 3-de( 2,6-dideoxy-3-C-methyl-3-O-methyl-α-L-ribo-hexopyranosyl)-oxy)-6-O-methyl- 3-oxo-erythromycin with a Rf=0.33 (EtIso-MeOH TEA 85-10-5).

EXAMPLE 52

(E) 9-O-(2-((3-1H-imidazol-1-yl)propyl)amino)-ethyl) oxime of -3-de(2,6-dideoxy-3-C-methyl-3-O-methyl-α-L-ribo-hexopyranosyl)-oxy)- 6-O-methyl-3-oxo-erythromycin with a Rf=0.4 (CHCl$_3$-MeOH-NH$_4$OH 90-10-1).

EXAMPLE 53

(E) 9-O-((2-piperidinyl)methyl)oxime de-3-de(2,6-dideoxy-3-C-methyl-3-O-methyl-α-L-ribo-hexopyranosyl)-oxy)-6-O-methyl-3-oxo erythromycin with a Rf=0.5 (AcOEt-MeOH-TEA 10-5-5).

EXAMPLE 54

(E) 9-O-((3-piperidinyl) oxime of -3-de(2,6-dideoxy-3-C-methyl- 3-O-methyl-α-L-ribo-hexopyranosyl)-oxy)-6-O-methyl-3-oxo-erythromycin Isomer A with a Rf=0.35 (CHCl$_3$-MeOH-NH$_4$OH 92-8-0.5).

EXAMPLE 55

(E) 9-O-((3-piperidinyl)oxime of -3-de(2,6-dideoxy-3-C-methyl- 3-O-methyl-α-L-ribo-hexopyranosyl)-oxy)-6-O-methyl-3-oxo-erythromycin Isomere B with a Rf=0.32 (CHCl$_3$-MeOH-NH$_4$OH 92-8-0.5).

EXAMPLE 56

(E) 9-O-(2-(methyl(2-propenyl)amino)ethyl)oxime of 3-de( 2,6-dideoxy-3-C-methyl-3-O-methyl-α-L-ribo-hexopyranosyl)-oxy)-6-O-methyl- 3-oxo-erythromycin melting at 164°–166° C.

EXAMPLE 57

(E) 9-O-(2-(methylamino)ethyl)oxime of 3-de(2,6-dideoxy- 3-C-methyl-3-O-methyl-α-L-ribo-hexopyranosyl)-oxy)-6-O-methyl-3-oxo-erythromycin melting at 163°–165° C.

EXAMPLE 58

(E) 9-O-(3-(1-(diphenylmethyl)azetidinyl)oxime of 3-de( 2,6-dideoxy-3-C-methyl-3-O-methyl-α-L-ribo-hexopyranosyl)-oxy)-6-O-methyl- 3-oxo-erythromycin with a Rf=0.2 (AcOEt-TEA 98-2).

EXAMPLE 59

(E) 9-O-((1-methyl-2-piperidinyl)methyl) oxime of 3-de( 2,6-dideoxy-3-C-methyl-3-O-methyl-α-L-ribo-hexopyranosyl)-oxy)-6-O-methyl- 3-oxo-erythromycin with a Rf=0.38 (AcOEt-TEA 95-5).

EXAMPLE 60

(E) 9-O-((1-azabicyclo(2.2.2)octan-3-yl) oxime of 3-de( 2,6-dideoxy-3-C-methyl-3-O-methyl-α-L-ribo-hexopyranosyl)-oxy)-6-O-methyl- 3-oxo-erythromycin (dioxalate) melting at 182°–184° C.

As examples of the products of formula I, the following products can be mentioned, corresponding to the products of the preceding examples, in which X and X' have the following meaning:

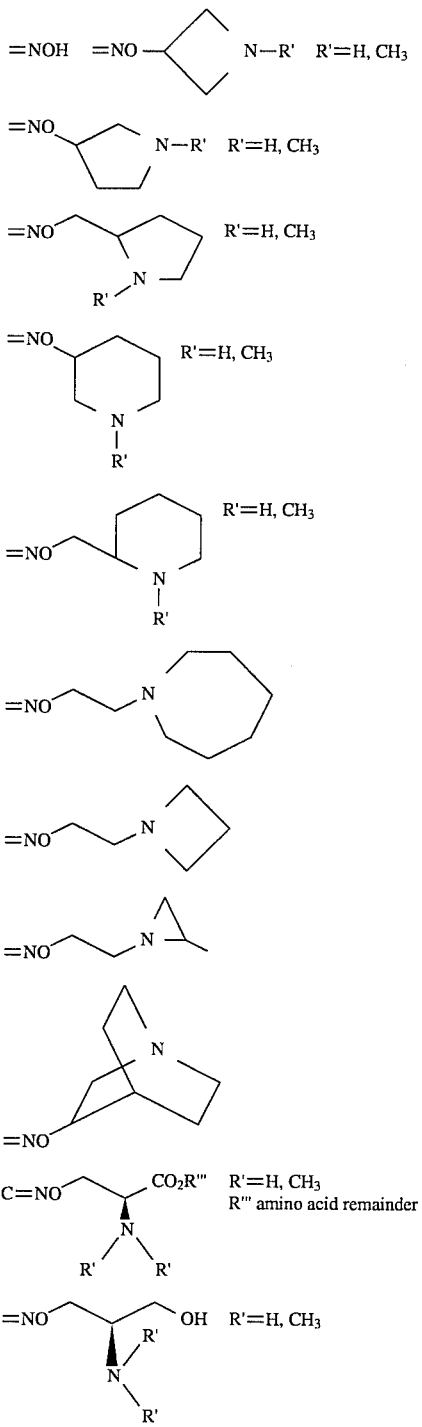

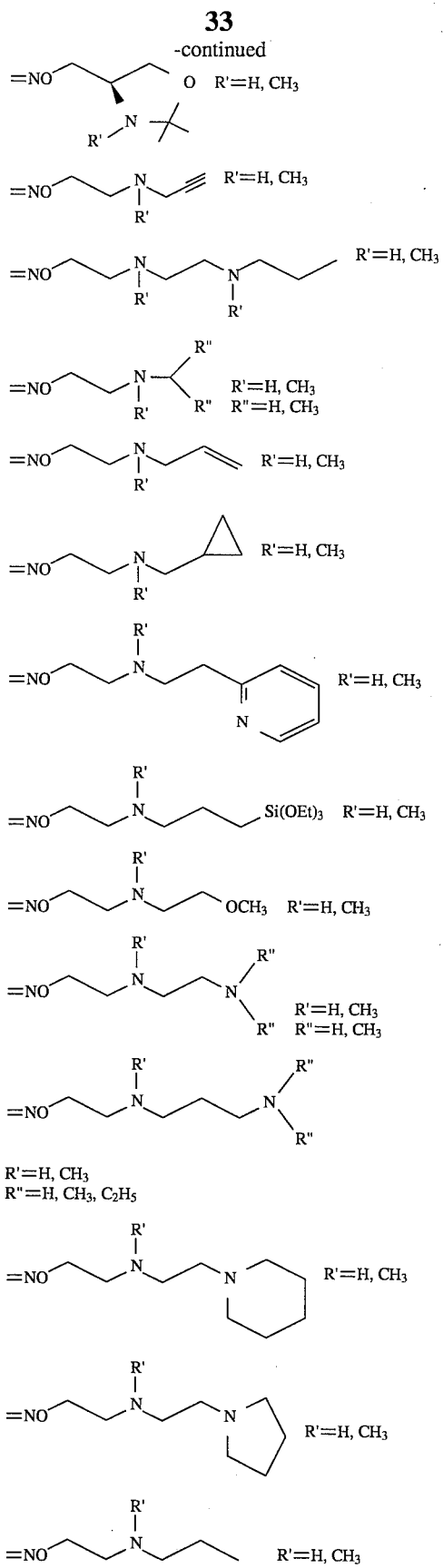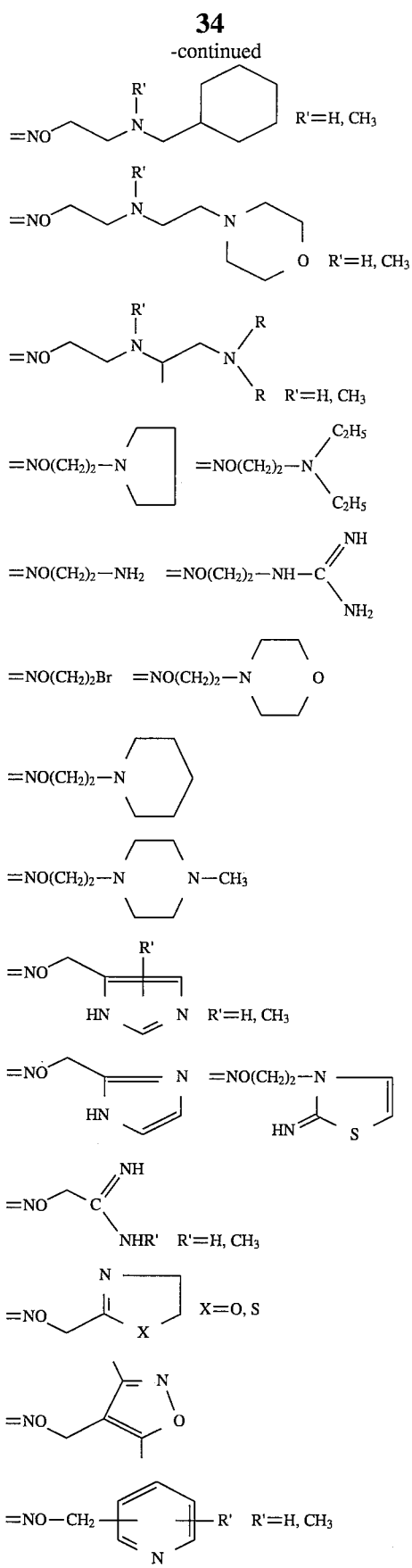

-continued

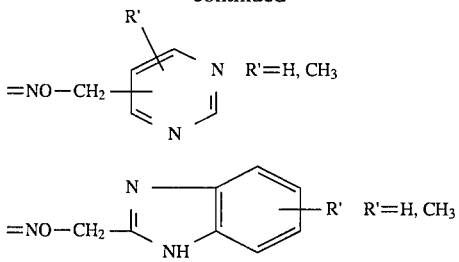

EXAMPLE 61

Tablets were prepared containing 150 mg of the product of Example 1 or 7 or 10 and sufficient excipient of starch, talc and magnesium stearate for a final weight of 1 g.

PHARMACOLOGICAL STUDY OF THE PRODUCTS OF THE INVENTION

A) Activity in vitro
Method of dilutions in liquid medium.

A series of tubes were prepared in which the same amount of sterile nutritive medium was distributed and increasing amounts of the product to be studied was distributed in each tube. Then, each tube was seeded with a bacterial strain and after incubating for twenty-four hours in an oven at 37° C., the inhibition of growth was determined by transillumination which allowed the minimum inhibiting concentrations (M.I.C.) to be evaluated expressed in micrograms/ml and the following results were obtained:

| Product of Example 1 | μg/ml after 24 hours |
|---|---|
| *Staphylococcus aureus* 011UC4 | 0.08 |
| *Staphylococcus aureus* 011HT17 | 0.08 |
| *Staphylococcus aureus* 011G025I | 1.2 |
| *Streptococcus pyogenes* group A 02A1UC11 | ≦0.01 |
| *Streptococcus agalactiae* group B 02B1HT1 | ≦0.01 |
| *Streptococcus* sp group C 02C0CB3 | 0.02 |
| *Streptococcus faecalis* group D 02D2UC1 | 0.04 |
| *Streptococcus faecium* group D 02D3HT1 | 0.04 |
| *Streptococcus sanguis* 02sgGR18 | ≦0.01 |
| *Streptococcus mitis* 02mitCB1 | 0.02 |
| *Streptococcus mitis* 02mitGR16 | 0.3 |
| *Streptococcus pneumoniae* 032UC1 | 0.15 |
| *Streptococcus pneumoniae* 030SJ1 | 2.5 |
| *Streptococcus pneumoniae* 030SJ5 | 0.15 |

| Product of Example 2 | μg/ml after 24 hours |
|---|---|
| *Staphylococcus aureus* 011UC4 | 0.3 |
| *Staphylococcus aureus* 011HT17 | 0.3 |
| *Staphylococcus aureus* 011G025I | 1.25 |
| *Streptococcus pyogenes* group A 02A1UC1 | 0.15 |
| *Streptococcus agalactiae* group B 02B1HT1 | 0.08 |
| *Streptococcus* sp group C 02C0CB3 | 0.3 |
| *Streptococcus faecalis* group D 02D2UC1 | 0.6 |
| *Streptococcus faecium* group D 02D3HT1 | 0.6 |
| *Streptococcus* sp group G 02G0GR5 | 0.3 |
| *Streptococcus sanguis* 02sgGR18 | 0.3 |
| *Streptococcus mitis* 02MitCB1 | 0.15 |
| *Streptococcus* sp group C 02C0CB1 | 5.0 |

| Product of Example 7 | μg/ml after 24 hours |
|---|---|
| *Staphylococcus aureus* 011UC4 | 0.15 |
| *Staphylococcus aureus* 011HT17 | 0.08 |
| *Staphylococcus aureus* 011G025I | 0.3 |
| *Streptococcus pyogenes* group A 02A1UC1 | ≦0.02 |
| *Streptococcus agalactiae* group B 02B1HT1 | ≦0.02 |
| *Streptococcus* sp group C 02C0CB3 | 0.04 |
| *Streptococcus faecalis* group D 02D2UC1 | 0.04 |
| *Streptococcus faecium* group D 02D3HT1 | 0.04 |
| *Streptococcus sanguis* 02sgGR18 | 2.5 |
| *Streptococcus mitis* 02mitCB1 | ≦0.02 |
| *Streptococcus pneumoniae* 032UC1 | ≦0.02 |
| *Streptococcus pneumoniae* 030SJ5 | 0.3 |

| Product of Example 10 | μg/ml after 24 hours |
|---|---|
| GRAM+ bacterial strains | |
| *Staphylococcus aureus* 011UC4 | 0.04 |
| *Staphylococcus aureus* 011HT17 | 0.04 |
| *Staphylococcus aureus* 011G025I | 0.04 |
| *Staphylococcus epidermidis* 012GO11C | 0.04 |
| *Streptococcus pyogenes* group A 02A1UC1 | ≦0.02 |
| *Streptococcus agalactiae* group B 02B1HT1 | ≦0.02 |
| *Streptococcus* sp group C 02C0CB3 | ≦0.02 |
| *Streptococcus faecalis* group D 02D2UC1 | ≦0.02 |
| *Streptococcus faecium* group D 02D3HT1 | ≦0.02 |
| *Streptococcus* sp group G 02G0GR5 | ≦0.02 |
| *Streptococcus sanguis* 02sgGR18 | 0.3 |
| *Streptococcus mitis* 02mitCB1 | ≦0.02 |
| *Streptococcus agalactiae* group B 02B1SJ1 | 0.3 |
| *Streptococcus* sp group C 02C0CB1 | 0.15 |
| *Streptococcus sanguis* 02sgGR10 | 0.08 |

| Product of Example 10 | µg/ml after 24 hours |
|---|---|
| *Streptococcus mitis* 02mitGR16 | 0.15 |
| *Streptococcus pneumoniae* 032UC1 | ≦0.02 |
| *Streptococcus pneumoniae* 030SJ1 | 0.3 |
| *Streptococcus pneumoniae* 030SJ5 | 0.04 |
| GRAM⁻ bacterial strains | |
| *Haemophilus influenzae* 351HT3 | 2.5 |
| *Haemophilus influenzae* 351CB12 | 2.5 |
| *Haemophilus influenzae* 351CA1 | 5 |
| *Haemophilus influenzae* 351GR6 | 5 |

| Product of Example 13 | µg/ml after 24 hours |
|---|---|
| GRAM⁺ bacterial strains | |
| *Staphylococcus aureus* 011UC4 | 0.3 |
| *Staphylococcus aureus* 011HT17 | 0.3 |
| *Staphylococcus aureus* 011GO25I | 1.2 |
| *Staphylococcus epidermidis* 012GO11C | 0.6 |
| *Streptococcus pyogenes* group A 02A1UC1 | 0.04 |
| *Streptococcus agalactiae* group B 02B1HT1 | <0.02 |
| *Streptococcus sp* group C 02C0CB3 | 0.08 |
| *Streptococcus faecalis* group D 02D2UC1 | 0.15 |
| *Streptococcus faecium* group D 02D3HT1 | 0.15 |
| *Streptococcus sp* group G 02G0GR5 | 0.04 |
| *Streptococcus sanguis* 02sgGR18 | ≦0.02 |
| *Streptococcus mitis* 02mitCB1 | 0.04 |
| *Streptococcus agalactiae* group B 02B1SJ1 | — |
| *Streptococcus sp* group C 02C0CB1 | — |
| *Streptococcus sanguis* 02sgGR10 | 2.5 |
| *Streptococcus mitis* 02mitGR16 | — |
| *Streptococcus pneumoniae* 032UC1 | — |
| *Streptococcus pneumoniae* 030SJ1 | 0.6 |
| *Streptococcus pneumoniae* 030SJ5 | 1.2 |

| Product of Example 36 | µg/ml after 24 hours |
|---|---|
| GRAM⁺ bacterial strains | |
| *Staphylococcus aureus* 011UC4 | 1.2 |
| *Staphylococcus aureus* 011HT17 | 0.3 |
| *Staphylococcus aureus* 011GO25I | — |
| *Staphylococcus epidermidis* 012GO11C | 2.5 |
| *Streptococcus pyogenes* group A 02A1UC1 | 0.15 |
| *Streptococcus agalactiae* group B 02B1HT1 | 0.04 |
| *Streptococcus sp* group C 02C0CB3 | 0.3 |
| *Streptococcus faecalis* group D 02D2UC1 | 0.3 |
| *Streptococcus faecium* group 02D3HT1 | 0.15 |
| *Streptococcus sp* group G 02G0GR5 | 0.3 |
| *Streptococcus sanguis* 02sgGR18 | — |
| *Streptococcus mitis* 02mitCB1 | 0.08 |
| *Streptococcus agalactiae* group B 02B1SJ1 | — |
| *Streptococcus sp* group C 02C0CB1 | — |
| *Streptococcus sanguis* 02sgGR10 | — |
| *Streptococcus mitis* 02mitGR16 | — |
| *Streptococcus pneumoniae* 032UC1 | 0.08 |
| *Streptococcus pneumoniae* 030SJ1 | — |
| *Streptococcus pneumoniae* 030SJ5 | — |

| Product of Example 37 | µg/ml after 24 hours |
|---|---|
| GRAM⁺ bacterial strains | |
| *Staphylococcus aureus* 011UC4 | 0.15 |
| *Staphylococcus aureus* 011HT17 | 0.08 |
| *Staphylococcus aureus* 011GO25I | — |
| *Staphylococcus epidermidis* 012GO11C | 0.15 |
| *Streptococcus pyogenes* group A 02A1UC1 | 0.04 |
| *Streptococcus agalactiae* group B 02B1HT1 | ≦0.02 |
| *Streptococcus sp* group C 02C0CB3 | 0.04 |
| *Streptococcus faecalis* group D 02D2UC1 | 0.08 |
| *Streptococcus faecium* group D 02D3HT1 | 0.08 |
| *Streptococcus sp* group G 02G0GR5 | 0.04 |
| *Streptococcus sanguis* 02sgGR18 | 1.2 |
| *Streptococcus mitis* 02mitCB1 | 0.04 |
| *Streptococcus agalactiae* group B 02B1SJ1 | 1.2 |
| *Streptococcus sp* group C 02C0CB1 | 1.2 |
| *Streptococcus sanguis* 02sgGR10 | 0.6 |
| *Streptococcus mitis* 02mitGR16 | 0.3 |
| *Streptococcus pneumoniae* 032UC1 | ≦0.02 |
| *Streptococcus pneumoniae* 030SJ1 | 2.5 |
| *Streptococcus pneumoniae* 030SJ5 | 0.3 |

B) In vivo Activity

Experimental infection with *Staphylococcus aureus*

The action of the product of Example 2 was studied by an experimental infection with *Staphylococcus aureus* on mice. Batches of ten male mice weighing from 18 to 20 g were infected by intraperitoneal injection of 0.5 ml of a 22 hour culture medium at pH 7 of the *Staphylococcus aureus* strain No. 54,146 diluted to ⅙ with physiological water. A determined amount of the product was administered orally at the time of infection and 4 hours after injection.

The following results were obtained:

| DOSE in mg | ANIMAL MORTALITY | | | SURVIVING AFTER 3 DAYS |
|---|---|---|---|---|
| | D1 24 h | D2 48 h | D3 72 h | |
| Control | 9 | | | 1/10 |
| 0.1 | 7 | 3 | | 0/10 |
| 0.3 | 1 | 1 | 2 | 6/10 |
| 1 | 0 | | | 10/10 |
| 3 | 0 | | | 10/10 |

$DP_{50}$ Total administration: 12.49 mg/kg (Reed and Muench method).

CONCLUSION

The products of the invention show a good antibiotic activity in vivo.

Various modifications of the products and method of the invention may be made without departing from the spirit or scope thereof and it should be understood that the invention is intended to be limited only as defined in the appended claims.

What is claimed is:

1. A compound of the formula

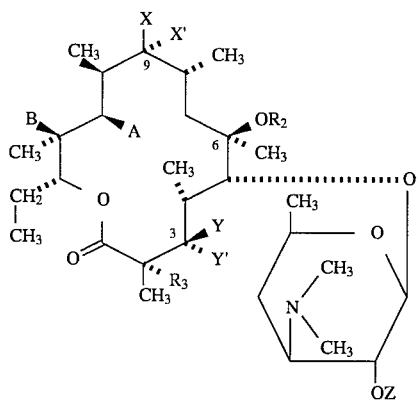

I wherein X and X' together with the carbon atom to which they are attached is —C=O or —C=NOR, R is

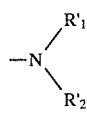

wherein $R'_1$ and $R'_2$ are individually selected from the group consisting of hydrogen, alkyl, cycloalkyl, alkenyl and alkynyl of up to 18 carbon atoms, phenyl, naphthyl and phenylalkyl of 1 to 4 alkyl carbon atoms, each of $R'_1$ and $R'_2$ being optionally substituted by at least one member of the group consisting of hydroxy, amino, monoalkylamino of up to 4 carbon atoms, dialkylamino of up to 8 carbon atoms, cyano, acyl and carbamoyl of up to 8 carbon atoms, Y and Y' together with the carbon atom are C=O, B is hydrogen or $OR_4$, $R_4$ is hydrogen or forms with A a carbonate or carbamate, A forms with the carbon which carries it and the carbon in position 10 a double bond, or A is —$OR'_4$, $R'_4$ is hydrogen, or forms with B a carbonate, or A is

, $R'_5$ is =C=O forming with B a carbamate group, $R'_6$ is hydrogen or alkyl, —$C_6H_5$—$(CH_2)_a$— or alkoxy of up to 12 carbon atoms, a is 1, 2, 3 or 4 or

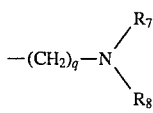

$R_7$ and $R_8$ are individually hydrogen or alkyl or —$C_6H_5$—$(CH_2)_a$— of up to 18 carbon atoms, q is an integer between 1 and 6, or A is

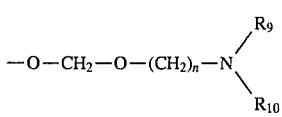

$R_9$ and $R_{10}$ are hydrogen or alkyl of 1 to 8 carbon atoms, n is an integer between 1 and 6, $R_2$ is selected from the group consisting of alkyl of 1 to 8 carbon atoms, —$CONH_2$, —$CONHCOR_{11}$ and —$CONHSO_2R_{11}$, $R_{11}$ is a hydrocarbon of 1 to 18 carbon atoms optionally containing at least one heteroatom, $R_3$ in α or β position is selected from the group consisting of a) hydrogen, b) alkyl of 1 to 8 carbon atoms, c)

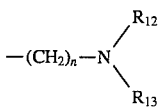

$R_{12}$ and $R_{13}$ are selected from the group consisting of hydrogen and alkyl of 1 to 8 carbon atoms, and d)

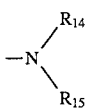

$R_{14}$ and $R_{15}$ are individually hydrogen or alkyl of 1 to 8 carbon atoms, Z is hydrogen or the remainder of a carboxylic acid of 1 to 18 carbon atoms, the oximes that can be represented by X and X' or Y and Y' can be of syn or anti configuration or its non-toxic, pharmaceutically acceptable acid addition salt.

2. A compound of claim 1 wherein X and X' together with carbon to which they are attached form >C=NOR.

3. A compound of claim 1 wherein X and $X_1$' together with the carbon to which they are attached are >C=O.

4. A compound of claim 1 wherein X and X' and Y and Y' together with the carbon to which they are attached are >C=O.

5. A compound of claim 1 wherein $R_2$ is alkyl of 1 to 4 carbon atoms.

6. A compound of claim 1 wherein $R_2$ is methyl.

7. A compound of claim 1 wherein $R_3$ is a β- or α-hydrogen.

8. A compound of claim 1 wherein A is —OH.

9. A compound of claim 1 wherein B is —OH.

10. A compound of claim 1 wherein A and B form a cyclic 11,12-carbonate.

11. A compound of claim 1 wherein A and B are

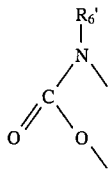

$R'_6$ is selected from the group consisting of hydrogen, alkyl, alkoxy and aralkyl of up to 12 carbon atoms and

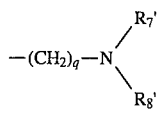

q is an integer of 1 to 6 and $R'_7$ and $R'_8$ are individually hydrogen or alkyl or phenylalkyl of up to 18 carbon atoms.

12. A compound of claim 11 wherein $R'_6$ is phenylalkyl of up to 12 carbon atoms.

13. A compound of claim 11 wherein $R'_6$ is $(CH_2)_4$—$C_6H_5$.

14. A compound of claim 1 wherein Z is hydrogen.

15. A compound of claim 1 selected from the group consisting of 9-[O-[2-(dimethylamino)-ethyl]-oxime] of 3-de[(2,6-dideoxy-3-C-methyl- 3-O-methyl-α-L-ribo-hexopyranosyl)-oxy]-6-O-methyl-3-oxo erythromycin, 11,12-dideoxy-3-de[(2,6-dideoxy-3-C-methyl-3-O-methyl-α-L-ribo-hexopyranosyl)-oxy]-6-O-methyl-3-oxo-12,11-[oxycarbonyl-[(4-phenylbutyl)-imino]] erythromycin, 9-[O-[(2-methoxy-ethoxy)-methyl]-oxime] of 3-de[(2,6-dideoxy-3-C-methyl-3-O-methyl-α-L-ribo-hexopyranosyl)-oxy]-6-O-methyl 3-oxo erythromycin, 3-de[(2,6-dideoxy-3-C-methyl-3-O-methyl-α-L-ribo-hexopyranosyl)-oxy]-6-O-methyl 3-oxo erythromycin, cyclic 11,12-carbonate of 3-de[(2,6-dideoxy-3-C-methyl-3-O-methyl-α-L-ribo-hexopyranosyl)-oxy]- 6-O-methyl 3-oxo erythromycin, (E) 9-O-[2-[[2-(1-pyrrolidinyl-ethyl]-amino]-ethyl]-oxime of 3-de[(2,6-dideoxy-3-C-methyl-3-O-methyl-α-L-ribo-hexopyranosyl)-oxy]-6-O-methyl 3-oxo-erythromycin 9-O-(3-piperidinyl)-oxime of 3-de[(2,6-dideoxy-3-C-methyl-3-O-methyl-α-L-ribo-hexopyranosyl)-oxy]-6-O-methyl-3-oxo-erythromycin, and (E) 9-O-[2-(dimethylamino)-ethyl]-oxime of 3-de[(2,6-dideoxy-3-C-methyl- 3-O-methyl-α-L-ribo-hexopyranosyl)-oxy]-11-deoxy-10,11-didehydro- 6-O-methyl 3-oxo-erythromycin.

16. An antibacterial composition comprising an antibactericidally efective amount of at least one compound of claim 1 and an inert pharmaceutical carrier.

17. A composition of claim 16 wherein in the compound X and X' together with carbon to which they are attached form >C=NOR.

18. A composition of claim 16 wherein in the compound X and X' together with the carbon to which they are attached form >C=O.

19. A method of treating bacterial infections in warm-blooded animals comprising administering to warm-blooded animals an antibactericidally effective amount of at least one compound of claim 1.

20. A method of claim 19 wherein in the compound X and X' together with carbon to which they are attached form >C=NOR.

21. A method of claim 19 wherein in the compound X and X' together with the carbon to which they are attached form >C=O.

22. The method of claim 19 wherein the active compound is selected from the group consisting of 9-[O-[2-(dimethylamino)-ethyl]]-oxime] of 3-de[(2,6-dideoxy-3-C-methyl-3-O-methyl-α-L-ribo-hexopyranosyl)-oxy]-6-O-methyl-3-oxoerythromycin, 11,12-dideoxy-3-de[(2,6-dideoxy-3-C-methyl-3-O-methyl-α-L-ribo-hexopyranosyl)-oxy]-6-O-methyl-3-oxo-12,11-[oxycarbonyl-[(4-phenylbutyl)-imino]] erythromycin, 9-[O-[(2-methoxy-ethoxy)-methyl]-oxime] of 3-de[(2,6-dideoxy-3-C-methyl-3-O-methyl-α-L-ribo-hexopyranosyl)-oxy]-6-O-methyl 3-oxo erythromycin, 3-de[(2,6-dideoxy- 3-C-methyl-3-O-methyl-α-L-ribo-hexopyranosyl)-oxy]-6-O-methyl 3-oxo erythromycin, cyclic 11,12-carbonate of 3-de[(2,6-dideoxy- 3-C-methyl-3-O-methyl-α-L-ribo-hexopyranosyl)-oxy]-6-O-methyl 3-oxo erythromycin, (E) 9-O-[2-[[2-(1-pyrrolidinyl-ethyl]-amino]-ethyl]-oxime of 3-de[(2,6-dideoxy-3-C-methyl-3-O-methyl-α-L-ribo-hexopyranosyl)-oxy]-6-O-methyl 3-oxo erythromycin, 9-O-(3-piperidinyl)-oxime of 3-de[(2,6-dideoxy-3-C-methyl-3-O-methyl-α-L-ribo-hexopyranosyl)-oxy]-6-O-methyl-3-oxo-erythromycin, and (E) 9-O-[2-(dimethylamino)-ethyl]-oxime of 3-de[(2,6-dideoxy-3-C-methyl-3-O-methyl-α-L-ribo-hexopyranosyl)-oxy]-11-deoxy-10,11-didehydro-6-O-methyl 3-oxo-erythromycin.

\* \* \* \* \*